(12) United States Patent
Lucas et al.

(10) Patent No.: US 8,119,344 B2
(45) Date of Patent: Feb. 21, 2012

(54) MUTATION IN THE REGULATORY REGION OF GJB2 MEDIATES NEONATAL HEARING LOSS WITHIN DFNB1

(75) Inventors: Trevor Lucas, Vienna (AT); Klemens Frei, Langenzersdorf (AT); Wolf-Dieter Baumgartner, Siegenfeld (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 315 days.

(21) Appl. No.: 12/389,134

(22) Filed: Feb. 19, 2009

(65) Prior Publication Data

US 2009/0226920 A1    Sep. 10, 2009

Related U.S. Application Data

(60) Provisional application No. 61/066,146, filed on Feb. 19, 2008.

(51) Int. Cl.
*C12Q 1/68* (2006.01)
*C12P 19/34* (2006.01)

(52) U.S. Cl. .................. 435/6.1; 435/6.11; 435/6.12

(58) Field of Classification Search .................. None
See application file for complete search history.

(56) References Cited

U.S. PATENT DOCUMENTS

| | | | | |
|---|---|---|---|---|
| H2153 H | 4/2006 | Ignar et al. | | 435/6 |
| 2004/0203035 A1 | 10/2004 | Mast et al. | | 435/6 |

OTHER PUBLICATIONS

Rothrock et al. Human Genetics (2003) 113:18-23.*
Maria Bitner-Glindzicz, Hereditary deafness and phenotyping in humans, British Medical Bulletin, vol. 63, pp. 73-94, 2002.
Sandrine Marlin, MD, PhD, et al., Connexin 26 Gen mutations in Congenitally Deaf Children, Arch Otolaryngol Head Neck Surg., vol. 127, pp. 927-933, Aug. 2001.
D. N. Cooper, Human gene mutation in pathology and evolution, J. Inherit. Metab. Dis. vol. 25, pp. 157-182, 2002.
Ahmad, et al., "*Post-translational integration and oligomerization of connexin 26 in plasma membranes and evidence of formation of membrane pores: implications for the assembly of gap junctions*," Biochem J., 365, pp. 693-699, 2002.
Barker, et al., "*Identification of mutations in the COL4A5 collagen gene in Alport syndrome*," Science 248, pp. 1224-1227, 1990.
Cartharius, et al., "*MatInspector and beyond: promoter analysis based on transcription factor binding sites*," Bioinformatics vol. 21, No. 13, pp. 2933-2942, 2005.
Cohen-Salmon, et al., "*Targeted ablation of connexin26 in the inner ear epithelial gap junction network causes hearing impairment and cell death*," Current Biology, vol. 12, 1106-1111, 2002.
Cristobal, et al., Article in Press: "*Assessment of differential gene expression in vestibular epithelial cell types using microarray analysis*," Brain Res Mol Brain Res 133, pp. 19-36, 2005.

Dahl, et al., "*Molecular cloning and functional expression of mouse connexin-30, a gap junction gene highly expressed in adult brain and skin*," J Biol Chem, vol. 271, pp. 17903-17910, 1996.
del Castillo, et al., "*A novel deletion involving the connexin-30 gene, del(GJB6-d13s1854), found in trans with mutations in the GJB2 gene (connexin-26) in subjects with DFNB1 non-syndromic hearing impairment*," J Med Genet vol. 42, pp. 588-594, 2005.
Denoyelle, et al., "*Prelingual deafness: high prevalence of a 30delG mutation in the connexin 26 gene*," Hum Mol Genet, vol. 6, No. 12, pp. 2173-2177, 1997.
Denoyelle, et al., "*Clinical features of the prevalent form of childhood deafness, DFNB1, due to a connexin-26 gene defect: implications for genetic counseling*," Lancet, vol. 353, pp. 1298-1303, 1999.
Emery, et al., "*A consensus motif in the RFX DNA binding domain and binding domain mutants with altered specificity*," Mol Cell Biol, vol. 16, No. 8, pp. 4486-4494, 1996.
Estivill, et al., "*Connexin-26 mutations in sporadic and inherited sensorineural deafness*," Lancet, vol. 351, pp. 394-398, 1998.
Falk, et al., "*Cell-free synthesis and assembly of connexins into functional gap junction membrane channels*," Embo J vol. 16, No. 10, pp. 2703-2716, 1997.
Filippov, et al., "*A reporter allele for investigating connexin 26 gene expression in the mouse brain*," Eur. J. Neurosci., vol. 18, pp. 3183-3192, 2003.
Finsterer, et al., "*Nuclear and Mitochondrial Genes Mutated in Nonsyndromic Impaired Hearing*," Int'l Journal of Pediatric Otorhinolaryngology, vol. 69, No. 5, pp. 621-647, 2005.
Fortnum, et al., "*Epidemiology of permanent childhood hearing impairment in Trent Region*," pp. 1985-1993. Br. J. Audiol., vol. 31, 409-446, 1997.
Frei, et al., "*Connexin 26 mutations in cases of sensorineural deafness in eastern Austria*," Eur J Hum Genet vol. 10, pp. 427-432, 2002.
Frei, et al., "GJB2 mutations in hearing impairment: identification of a broad clinical spectrum for improved genetic counseling," Laryngoscope vol. 115, pp. 461-465, 2005.
Higashi, et al., "*Impairment of T cell development in δEF1 mutant mice*," J Exp Med vol. 185, No. 8, pp. 1467-1479, 1997.
Hirokawa, et al., "*SOSUI: classification and secondary structure prediction system for membrane proteins*," Bioinformatics vol. 14, No. 4, pp. 378-379, 1998.

(Continued)

*Primary Examiner* — Juliet Switzer
(74) *Attorney, Agent, or Firm* — Sunstein Kann Murphy & Timbers LLP

(57) ABSTRACT

Homozygous alterations in the gap junction protein GJB2 (connexin 26), within the DFNB1 locus, are responsible for up to 50% of autosomal recessive non-syndromic hearing impairment (NSHI). Analysis of the GJB2 promoter revealed the potential importance of T-228C in the regulation of GJB2 expression. Of regulatory factors known to be expressed in the inner ear, the T-228C transition would delete potential binding sites for the X-box binding protein (RFX1) and the H6 homeobox 3 (HMX3/Nkx5.1) transcription factor which has been linked to hearing impairment. These results suggest that T-228C may represent the most common mutation associated with development of NSHI in Caucasian populations identified to date and should be included in worldwide newborn screening programs for NSHI.

17 Claims, 2 Drawing Sheets

OTHER PUBLICATIONS

Houseman, et al., "*Genetic analysis of the connexin-26 M34T variant: identification of genotype M34T/M34T segregating with mild-moderate non-syndromic sensorineural hearing loss,*" J. Med. Genet., vol. 38, pp. 20-25, 2001.

Ikeda, et al., "*DNA binding through distinct domains of zinc-finger-homeodomain protein AREB6 has different effects on gene transcription,*" Eur. J. Biochem. vol. 233, pp. 73-82, 1995.

Kalay, et al., "*GJB2 Mutations in Turkish Patients with ARNSHL: Prevalence and Two Novel Mutations,*" Hearing Research, vol. 203, No. 1-2, pp. 88-93, 2005.

Kelsell, et al., "*Connexin 26 mutations in hereditary non-syndromic sensorineural deafness,*" Nature, vol. 387, pp. 80-83, 1997.

Kiang, et al., "*Upstream genomic sequence of the human connexin26 gene,*" Gene, vol. 199, pp. 165-171, 1997.

Krafchak, et al., "*Mutations in TCF8 cause posterior polymorphous corneal dystrophy and ectopic expression of COL4A3 by corneal endothelial cells,*" Am. J. Hum. Genet., vol. 77, pp. 694-708, 2005.

Kudo, et al., "*Transgenic expression of a dominant-negative connexin26 causes degeneration of the organ of Corti and non-syndromic deafness,*" Hum. Mol. Genet., vol. 12, No. 9, pp. 995-1004, 2003.

Ma, et al., "*The transcription factor regulatory factor X1 increases the expression of neuronal glutamate transporter type 3,*" J. Biol. Chem., vol. 281, No. 30, pp. 21250-21255, 2006.

Morris, et al., "*Upstream open reading frames as regulators of mRNA translation,*" Mol. Cell. Biol., vol. 20, No. 23, pp. 8635-8642, 2000.

Morton, N.E., "*Genetic epidemiology of hearing impairment,*" Ann. N.Y. Acad. Sci., vol. 630, pp. 16-31, 1991.

Murgia, et al., "*Cx26 deafness: mutation analysis and clinical variability,*" J. Med. Genet., vol. 36, 829-832, 1999.

Rinkwitz-Brandt, et al., "*Distinct temporal expression of mouse Nkx-5.1 and Nkx-5.2 homeobox genes during brain and ear development,*" Mech. Dev., vol. 52, 371-381, 1995.

Rothrock, et al., "*Connexin 26 35delG does not represent a mutational hotspo,*" Hum. Genet. vol. 113, pp. 18-23, 2003.

Scott, et al., "Identification of mutations in the connexin 26 gene that cause autosomal recessive nonsyndromic hearing loss,". Hum. Mutat., vol. 11, pp. 387-394, 1998.

Seeman, et al., "*High prevalence of the IVS 1 + 1 G to A/GJB2 mutation among Czech hearing impaired patients with monoallelic mutation in the coding region of GJB2,*" Clin. Genet.. vol. 69, pp. 410-413, 2006.

Segretain, et al., "*Regulation of connexin biosynthesis, assembly, gap junction formation, and removal. Biochim Biophys Acta,*" vol. 1662, pp. 3-21, 2004.

Smith, et al., "*Relationships Between Neurologic Disorders and Hereditary Hearing Loss,*" Seminars in Pediatric Neurology, vol. 8, No. 3, pp. 147-159, 2003.

Thiagalingam, et al., "*RREB-1, a novel zinc finger protein, is involved in the differentiation response to Ras in human medullary thyroid carcinomas,*" Mol. Cell. Biol., vol. 16, No. 10, pp. 5335-5345, 1996.

Tu, et al., "*Mapping and characterization of the basal promoter of the human connexin26 gene. Biochi.m Biophys,*" Acta., vol. 1443, pp. 169-181, 1998.

Van Laer, et al., "*A common founder for the 35delG GJB2 gene mutation in connexin 26 hearing impairment,*" J. Med. Genet., vol. 38, pp. 515-518, 2001.

Wang, et al., "*Hmx2 and Hmx3 homeobox genes direct development of the murine inner ear and hypothalamus and can be functionally replaced by Drosophila Hmx,*" Dev. Cell., vol. 7, pp. 439-453, 2004.

Watanabe, et al., "*Transcription factors positively and negatively regulating the Na,K-ATPase alpha 1 subunit gene,*" J. Biochem. (Tokyo) vol. 114, pp. 849-855, 1993.

Zelante, et al., "*Connexin26 mutations associated with the most common form of non-syndromic neurosensory autosomal recessive deafness (DFNB1) in Mediterranean,*". Hum. Mol. Genet., vol. 6, No. 9, pp. 1605-1609, 1997.

European Patent Office; Authorized Officer: Garganta M. Brochado, *Notification of Transmittal of the International Search Report and Written Opinion*; PCT/US2009/034523, dated May 25, 2009, 15 pages.

* cited by examiner

```
                        SEQUENCE LISTING

<160> NUMBER OF SEQ ID NOS: 74

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cgcactatgc ggagtacaga                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggtggcagtg ggtcaagtag                                              20

<210> SEQ ID NO 3
<211> LENGTH: 19
<212> TYPE: DNA
<213> ORGANISM: Artificial Sequence
<220> FEATURE:
<221> NAME/KEY: misc_feature
<222> LOCATION: (19)...(19)
<223> OTHER INFORMATION: N=A, G, C or T
<223> OTHER INFORMATION: primer

<400> SEQUENCE: 3
gcccccatga gttccccan                                               19

<210> SEQ ID NO 4
<211> LENGTH: 20
<212> TYPE: DNA
<213> ORGANISM: Artificial Sequence
<220> FEATURE:
<221> NAME/KEY: misc_feature
<222> LOCATION: (20)...(20)
<223> OTHER INFORMATION: N=A, G, C or T
<223> OTHER INFORMATION: primer

<400> SEQUENCE: 4
agcccccatg agttccccan                                              20
```

<210> SEQ ID NO 5
<211> LENGTH: 30
<212> TYPE: DNA
<213> ORGANISM: Artificial Sequence
<220> FEATURE:
<223> OTHER INFORMATION: probe

<400> SEQUENCE: 5
ccagcgatga gttccccaag tgcccgctgg                              30

<210> SEQ ID NO 6
<211> LENGTH: 30
<212> TYPE: DNA
<213> ORGANISM: Artificial Sequence
<220> FEATURE:
<223> OTHER INFORMATION: probe

<400> SEQUENCE: 6
ccagcgatga gttccccagg tgcccgctgg                              30

<210> SEQ ID NO 7
<211> LENGTH: 39
<212> TYPE: DNA
<213> ORGANISM: Artificial Sequence
<220> FEATURE:
<223> OTHER INFORMATION: probe

<400> SEQUENCE: 7
ctcctagttc ctttgagccc gcacttgggg aactcatgg                    39

<210> SEQ ID NO 8
<211> LENGTH: 39
<212> TYPE: DNA
<213> ORGANISM: Artificial Sequence
<220> FEATURE:
<223> OTHER INFORMATION: probe

<400> SEQUENCE: 8
ctcctagttc ctttgagccc gcacctgggg aactcatgg                    39

<210> SEQ ID NO 9
<211> LENGTH: 207
<212> TYPE: DNA
<213> ORGANISM: human

<400> SEQUENCE: 9
cgcttcctgg ggggtcccga ctctcagccg ccccgcttc acccgggccg ccaagggct    60 gggggaggcg gcgctcgggg taaccggggg agactcaggg cgctggggc acttggggaa   120 ctcatggggg ctcaaaggaa ctaggagatc gggacctcga aggggacttg ggggttcgg   180 ggctttcggg ggcggtcggg ggttcgc                                     207

<210> SEQ ID NO 10
<211> LENGTH: 207
<212> TYPE: DNA
<213> ORGANISM: human
<220> FEATURE:
<221> NAME/KEY: mutation
<222> LOCATION: (113)...(113)
<223> OTHER INFORMATION: T-->C transition

<400> SEQUENCE: 10
cgcttcctgg ggggtcccga ctctcagccg ccccgcttc acccgggccg ccaagggct    60 gggggaggcg gcgctcgggg taaccggggg agactcaggg cgctggggc acctggggaa   120

```
ctcatggggg ctcaaaggaa ctaggagatc gggacctcga agggacttg gggggttcgg    180 ggctttcggg ggcggtcggg ggttcgc                                        207

<210> SEQ ID NO 11
<211> LENGTH: 16
<212> TYPE: DNA
<213> ORGANISM: Artificial Sequence
<220> FEATURE:
<223> OTHER INFORMATION: probe

<400> SEQUENCE: 11
ggcacttggg gaactc                                                    16

<210> SEQ ID NO 12
<211> LENGTH: 16
<212> TYPE: DNA
<213> ORGANISM: Artificial Sequence
<220> FEATURE:
<223> OTHER INFORMATION: probe

<400> SEQUENCE: 12
ggcacctggg gaactc                                                    16

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
ccgcgagccc cattggcccc ctctgagtcc cgcg                                34

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
cccccgagtt tccttgatcc tctagccctg g                                   31

<210> SEQ ID NO 15
<211> LENGTH: 16
<212> TYPE: DNA
<213> ORGANISM: Artificial Sequence
<220> FEATURE:
<223> OTHER INFORMATION: probe

<400> SEQUENCE: 15
ctgggggcac ttgggg                                                    16

<210> SEQ ID NO 16
<211> LENGTH: 16
<212> TYPE: DNA
<213> ORGANISM: Artificial Sequence
<220> FEATURE:
<223> OTHER INFORMATION: probe

<400> SEQUENCE: 16
ctgggggcac ctgggg                                                    16

<210> SEQ ID NO 17
<211> LENGTH: 30
```

```
<212> TYPE: DNA
<213> ORGANISM: Artificial Sequence
<220> FEATURE:
<223> OTHER INFORMATION: primer

<400> SEQUENCE: 17
ccgcgagccc cattggcccc ctctgagtcc                                    30

<210> SEQ ID NO 18
<211> LENGTH: 34
<212> TYPE: DNA
<213> ORGANISM: Artificial Sequence
<220> FEATURE:
<223> OTHER INFORMATION: primer

<400> SEQUENCE: 18
cccccgagtt tccttgatcc tctagccctg gagc                               34

<210> SEQ ID NO 19
<211> LENGTH: 20
<212> TYPE: DNA
<213> ORGANISM: Artificial Sequence
<220> FEATURE:
<223> OTHER INFORMATION: probe

<400> SEQUENCE: 19
gggcacttgg ggaactcatg                                               20

<210> SEQ ID NO 20
<211> LENGTH: 20
<212> TYPE: DNA
<213> ORGANISM: Artificial Sequence
<220> FEATURE:
<223> OTHER INFORMATION: probe

<400> SEQUENCE: 20
gggcacctgg ggaactcatg                                               20

<210> SEQ ID NO 21
<211> LENGTH: 37
<212> TYPE: DNA
<213> ORGANISM: Artificial Sequence
<220> FEATURE:
<223> OTHER INFORMATION: primer

<400> SEQUENCE: 21
ccgccgcgag ccccattggc ccctctgag tcccgcg                             37

<210> SEQ ID NO 22
<211> LENGTH: 35
<212> TYPE: DNA
<213> ORGANISM: Artificial Sequence
<220> FEATURE:
<223> OTHER INFORMATION: primer

<400> SEQUENCE: 22
gagtttcctt gatcctctag ccctggagct tcccc                              35

<210> SEQ ID NO 23
<211> LENGTH: 19
<212> TYPE: DNA
<213> ORGANISM: Artificial Sequence
<220> FEATURE:
<223> OTHER INFORMATION: probe

<400> SEQUENCE: 23
gggcgctggg ggcacttgg                                                19
```

<210> SEQ ID NO 24
<211> LENGTH: 19
<212> TYPE: DNA
<213> ORGANISM: Artificial Sequence
<220> FEATURE:
<223> OTHER INFORMATION: probe

<400> SEQUENCE: 24
gggcgctggg ggcacctgg                                              19

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25 cccctccgc cgcgagcccc attggccccc tctg                              34

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26 gagtacccc gagtttcctt gatcctctag ccc                               33

<210> SEQ ID NO 27
<211> LENGTH: 15
<212> TYPE: DNA
<213> ORGANISM: Artificial Sequence
<220> FEATURE:
<223> OTHER INFORMATION: probe

<400> SEQUENCE: 27
ttccccaagt gcccc                                                  15

<210> SEQ ID NO 28
<211> LENGTH: 15
<212> TYPE: DNA
<213> ORGANISM: Artificial Sequence
<220> FEATURE:
<223> OTHER INFORMATION: probe

<400> SEQUENCE: 28
ttccccaggt gcccc                                                  15

<210> SEQ ID NO 29
<211> LENGTH: 17
<212> TYPE: DNA
<213> ORGANISM: Artificial Sequence
<220> FEATURE:
<223> OTHER INFORMATION: primer

<400> SEQUENCE: 29
tcctagttcc tttgagc                                                17

<210> SEQ ID NO 30
<211> LENGTH: 14
<212> TYPE: DNA
<213> ORGANISM: Artificial Sequence
<220> FEATURE:
<223> OTHER INFORMATION: primer

```
<400> SEQUENCE: 30
gggtcccgac tctc                                                      14

<210> SEQ ID NO 31
<211> LENGTH: 19
<212> TYPE: DNA
<213> ORGANISM: Artificial Sequence
<220> FEATURE:
<223> OTHER INFORMATION: primer

<400> SEQUENCE: 31
atctcctagt tcctttgag                                                 19

<210> SEQ ID NO 32
<211> LENGTH: 14
<212> TYPE: DNA
<213> ORGANISM: Artificial Sequence
<220> FEATURE:
<223> OTHER INFORMATION: primer

<400> SEQUENCE: 32
cgctcggggt aacc                                                      14

<210> SEQ ID NO 33
<211> LENGTH: 16
<212> TYPE: DNA
<213> ORGANISM: Artificial Sequence
<220> FEATURE:
<223> OTHER INFORMATION: primer

<400> SEQUENCE: 33
cctagttcct ttgagc                                                    16

<210> SEQ ID NO 34
<211> LENGTH: 13
<212> TYPE: DNA
<213> ORGANISM: Artificial Sequence
<220> FEATURE:
<223> OTHER INFORMATION: primer

<400> SEQUENCE: 34
ggggtcccga ctc                                                       13

<210> SEQ ID NO 35
<211> LENGTH: 18
<212> TYPE: DNA
<213> ORGANISM: Artificial Sequence
<220> FEATURE:
<223> OTHER INFORMATION: primer

<400> SEQUENCE: 35
ctcctagttc ctttgagc                                                  18

<210> SEQ ID NO 36
<211> LENGTH: 14
<212> TYPE: DNA
<213> ORGANISM: Artificial Sequence
<220> FEATURE:
<223> OTHER INFORMATION: primer

<400> SEQUENCE: 36
cgctcggggt aacc                                                      14

<210> SEQ ID NO 37
<211> LENGTH: 17
```

-continued

<212> TYPE: DNA
<213> ORGANISM: Artificial Sequence
<220> FEATURE:
<223> OTHER INFORMATION: probe

<400> SEQUENCE: 37
agttccccaa gtgcccc                                                      17

<210> SEQ ID NO 38
<211> LENGTH: 17
<212> TYPE: DNA
<213> ORGANISM: Artificial Sequence
<220> FEATURE:
<223> OTHER INFORMATION: probe

<400> SEQUENCE: 38
agttccccag gtgcccc                                                      17

<210> SEQ ID NO 39
<211> LENGTH: 17
<212> TYPE: DNA
<213> ORGANISM: Artificial Sequence
<220> FEATURE:
<223> OTHER INFORMATION: primer

<400> SEQUENCE: 39
tcctagttcc tttgagc                                                      17

<210> SEQ ID NO 40
<211> LENGTH: 14
<212> TYPE: DNA
<213> ORGANISM: Artificial Sequence
<220> FEATURE:
<223> OTHER INFORMATION: primer

<400> SEQUENCE: 40
gggtcccgac tctc                                                         14

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41
atctcctagt tcctttgag                                                    19

<210> SEQ ID NO 42
<211> LENGTH: 14
<212> TYPE: DNA
<213> ORGANISM: Artificial Sequence
<220> FEATURE:
<223> OTHER INFORMATION: primer

<400> SEQUENCE: 42
cgctcggggt aacc                                                         14

<210> SEQ ID NO 43
<211> LENGTH: 16
<212> TYPE: DNA
<213> ORGANISM: Artificial Sequence
<220> FEATURE:
<223> OTHER INFORMATION: primer

<400> SEQUENCE: 43
cctagttcct ttgagc                                                       16

<210> SEQ ID NO 44
<211> LENGTH: 13
<212> TYPE: DNA
<213> ORGANISM: Artificial Sequence
<220> FEATURE:
<223> OTHER INFORMATION: primer

<400> SEQUENCE: 44
ggggtcccga ctc                                                        13

<210> SEQ ID NO 45
<211> LENGTH: 18
<212> TYPE: DNA
<213> ORGANISM: Artificial Sequence
<220> FEATURE:
<223> OTHER INFORMATION: primer

<400> SEQUENCE: 45
ctcctagttc ctttgagc                                                   18

<210> SEQ ID NO 46
<211> LENGTH: 14
<212> TYPE: DNA
<213> ORGANISM: Artificial Sequence
<220> FEATURE:
<223> OTHER INFORMATION: primer

<400> SEQUENCE: 46
cgctcggggt aacc                                                       14

<210> SEQ ID NO 47
<211> LENGTH: 14
<212> TYPE: DNA
<213> ORGANISM: Artificial Sequence
<220> FEATURE:
<223> OTHER INFORMATION: probe

<400> SEQUENCE: 47
ttccccaagt gccc                                                       14

<210> SEQ ID NO 48
<211> LENGTH: 14
<212> TYPE: DNA
<213> ORGANISM: Artificial Sequence
<220> FEATURE:
<223> OTHER INFORMATION: probe

<400> SEQUENCE: 48
ttccccaggt gccc                                                       14

<210> SEQ ID NO 49
<211> LENGTH: 18
<212> TYPE: DNA
<213> ORGANISM: Artificial Sequence
<220> FEATURE:
<223> OTHER INFORMATION: primer

<400> SEQUENCE: 49
gatctcctag ttcctttg                                                   18

<210> SEQ ID NO 50
<211> LENGTH: 14
<212> TYPE: DNA
<213> ORGANISM: Artificial Sequence
<220> FEATURE:
<223> OTHER INFORMATION: primer

```
<400> SEQUENCE: 50
gggtcccgac tctc                                                    14

<210> SEQ ID NO 51
<211> LENGTH: 17
<212> TYPE: DNA
<213> ORGANISM: Artificial Sequence
<220> FEATURE:
<223> OTHER INFORMATION: primer

<400> SEQUENCE: 51
tcctagttcc tttgagc                                                 17

<210> SEQ ID NO 52
<211> LENGTH: 14
<212> TYPE: DNA
<213> ORGANISM: Artificial Sequence
<220> FEATURE:
<223> OTHER INFORMATION: primer

<400> SEQUENCE: 52
gggtcccgac tctc                                                    14

<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
atctcctagt tcctttgag                                               19

<210> SEQ ID NO 54
<211> LENGTH: 14
<212> TYPE: DNA
<213> ORGANISM: Artificial Sequence
<220> FEATURE:
<223> OTHER INFORMATION: primer

<400> SEQUENCE: 54
cgctcggggt aacc                                                    14

<210> SEQ ID NO 55
<211> LENGTH: 19
<212> TYPE: DNA
<213> ORGANISM: Artificial Sequence
<220> FEATURE:
<223> OTHER INFORMATION: primer

<400> SEQUENCE: 55
tctcctagtt cctttgagc                                               19

<210> SEQ ID NO 56
<211> LENGTH: 13
<212> TYPE: DNA
<213> ORGANISM: Artificial Sequence
<220> FEATURE:
<223> OTHER INFORMATION: primer

<400> SEQUENCE: 56
ccgggccgcc aag                                                     13

<210> SEQ ID NO 57
<211> LENGTH: 16
```

<212> TYPE: DNA
<213> ORGANISM: Artificial Sequence
<220> FEATURE:
<223> OTHER INFORMATION: primer

<400> SEQUENCE: 57
cctagttcct ttgagc                                                      16

<210> SEQ ID NO 58
<211> LENGTH: 13
<212> TYPE: DNA
<213> ORGANISM: Artificial Sequence
<220> FEATURE:
<223> OTHER INFORMATION: primer

<400> SEQUENCE: 58
ggggtcccga ctc                                                         13

<210> SEQ ID NO 59
<211> LENGTH: 18
<212> TYPE: DNA
<213> ORGANISM: Artificial Sequence
<220> FEATURE:
<223> OTHER INFORMATION: primer

<400> SEQUENCE: 59
ctcctagttc ctttgagc                                                    18

<210> SEQ ID NO 60
<211> LENGTH: 14
<212> TYPE: DNA
<213> ORGANISM: Artificial Sequence
<220> FEATURE:
<223> OTHER INFORMATION: primer

<400> SEQUENCE: 60
cgctcggggt aacc                                                        14

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
ccgatctcct agttcctttg                                                  20

<210> SEQ ID NO 62
<211> LENGTH: 13
<212> TYPE: DNA
<213> ORGANISM: Artificial Sequence
<220> FEATURE:
<223> OTHER INFORMATION: primer

<400> SEQUENCE: 62
ccgggccgcc aag                                                         13

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
atctcctagt tcctttgagc                                                  20

```
<210> SEQ ID NO 64
<211> LENGTH: 15
<212> TYPE: DNA
<213> ORGANISM: Artificial Sequence
<220> FEATURE:
<223> OTHER INFORMATION: primer

<400> SEQUENCE: 64
cgctcggggt aaccg                                                    15

<210> SEQ ID NO 65
<211> LENGTH: 18
<212> TYPE: DNA
<213> ORGANISM: Artificial Sequence
<220> FEATURE:
<223> OTHER INFORMATION: primer

<400> SEQUENCE: 65
gatctcctag ttcctttg                                                 18

<210> SEQ ID NO 66
<211> LENGTH: 13
<212> TYPE: DNA
<213> ORGANISM: Artificial Sequence
<220> FEATURE:
<223> OTHER INFORMATION: primer

<400> SEQUENCE: 66
ggggtcccga ctc                                                      13

<210> SEQ ID NO 67
<211> LENGTH: 70
<212> TYPE: DNA
<213> ORGANISM: human

<400> SEQUENCE: 67
taaccggggg agactcaggg cgctgggggc acttggggaa ctcatggggg ctcaaaggaa   60
ctaggagatc                                                          70

<210> SEQ ID NO 68
<211> LENGTH: 70
<212> TYPE: DNA
<213> ORGANISM: human
<220> FEATURE:
<221> NAME/KEY: mutation
<222> LOCATION: (33)...(33)
<223> OTHER INFORMATION: T-->C transition

<400> SEQUENCE: 68
taaccggggg agactcaggg cgctgggggc acctggggaa ctcatggggg ctcaaaggaa   60
ctaggagatc                                                          70

<210> SEQ ID NO 69
<211> LENGTH: 13
<212> TYPE: DNA
<213> ORGANISM: Artificial Sequence
<220> FEATURE:
<223> OTHER INFORMATION: probe

<400> SEQUENCE: 69
ggggcacttg ggg                                                      13

<210> SEQ ID NO 70
<211> LENGTH: 15
```

```
<212> TYPE: DNA
<213> ORGANISM: Artificial Sequence
<220> FEATURE:
<223> OTHER INFORMATION: probe

<400> SEQUENCE: 70
tgggggcact tgggg                                              15

<210> SEQ ID NO 71
<211> LENGTH: 19
<212> TYPE: DNA
<213> ORGANISM: Artificial Sequence
<220> FEATURE:
<223> OTHER INFORMATION: probe

<400> SEQUENCE: 71
ggggcacttg gggaactca                                          19

<210> SEQ ID NO 72
<211> LENGTH: 13
<212> TYPE: DNA
<213> ORGANISM: Artificial Sequence
<220> FEATURE:
<223> OTHER INFORMATION: probe

<400> SEQUENCE: 72
ggggcacctg ggg                                                13

<210> SEQ ID NO 73
<211> LENGTH: 15
<212> TYPE: DNA
<213> ORGANISM: qArtificial Sequence
<220> FEATURE:
<223> OTHER INFORMATION: probe

<400> SEQUENCE: 73
gggggcacct gggga                                              15

<210> SEQ ID NO 74
<211> LENGTH: 15
<212> TYPE: DNA
<213> ORGANISM: Artificial Sequence
<220> FEATURE:
<223> OTHER INFORMATION: probe

<400> SEQUENCE: 74
gctgggggca cctgg                                              15
```

MUTATION IN THE REGULATORY REGION OF GJB2 MEDIATES NEONATAL HEARING LOSS WITHIN DFNB1

CROSS-REFERENCE TO RELATED APPLICATIONS

This application claims priority from U.S. Provisional Application No. 61/066,146 filed Feb. 19, 2008, hereby incorporated by reference herein in its entirety.

SEQUENCE LISTING APPENDIX

The sequences described in the specification, namely SEQ ID NO: 1 through SEQ ID NO:74, and disclosed in the "Sequence Listing" are being submitted with this application via the USPTO electronic filing system (EFS) in a text file named "1941_B22SeqListCopy1.txt" (prepared Feb. 19, 2009—13 kb total), along with a Sequence Table in a text file named "SequenceTable1941_B22.txt" (prepared Feb. 19, 2009—3.47 kb), in compliance with 37 CFR. §1.52(e) and §1.821(c) and are hereby incorporated by reference herein in their entirety.

TECHNICAL FIELD AND BACKGROUND ART

The present invention relates to genetic mutations in the promoter and coding regions for the gap junction protein beta 2 (GJB2) associated the recessive DFNB1 locus on chromosome 13, associations of such mutations with non-syndromic hearing impairment (NSHI), and genetic testing in humans for NSHI.

Introduction

Non-syndromic hearing impairment (NSHI) affects almost 1 in 2000 newborn children and is predominantly inherited in an autosomal recessive fashion (Fortnum and Davis, 1997, Epidemiology of permanent childhood hearing impairment in Trent Region, 1985-1993. Br J Audiol 31, 409-446; Morton, 1991, Genetic epidemiology of hearing impairment. Ann N Y Acad Sci 630, 16-31). Within the recessive DFNB1 locus on chromosome 13, alterations in the gap junction proteins beta 2 (GJB2) encoding Connexin 26 (Cx26) and GJB6 (Cx30) are known to cause sensorineural deafness (Denoyelle et al., 1997, Prelingual deafness: high prevalence of a 30delM mutation in the connexin 26 gene. Hum Mol Genet 6, 2173-2177; Kelsell et al., 1997, Connexin 26 mutations in hereditary non-syndromic sensorineural deafness. Nature 387, 80-83). Mutations in GJB2 are the most common associated with up to 50% of NSHI cases (Denoyelle et al., 1997, Prelingual deafness: high prevalence of a 30delG mutation in the connexin 26 gene. Hum Mol Genet 6, 2173-2177; Estivill et al., 1998, Connexin-26 mutations in sporadic and inherited sensorineural deafness. Lancet 351, 394-398) and are routinely assessed in the clinical analysis of genetic hearing impairment. Both targeted ablation and expression of mutant connexins causes hearing loss by impairment of $K^+$ homeostasis within supporting cells during development leading to degradation of the organ of corti (Cohen-Salmon et al., 2002, Targeted ablation of connexin26 in the inner ear epithelial gap junction network causes hearing impairment and cell death. Curr Biol 12, 1106-1111; Kudo et al., 2003, Transgenic expression of a dominant-negative connexin26 causes degeneration of the organ of Corti and non-syndromic deafness. Hum Mol Genet 12, 995-1004).

The most frequent GJB2 mutation in Caucasian populations is the frameshift deletion of a guanine residue at position 35 of the normal coding sequence (35delG) which leads to the introduction of a premature stop codon after base pairs 37-39 (Zelante et al., 1997, Connexin26 mutations associated with the most common form of non-syndromic neurosensory autosomal recessive deafness (DFNB1) in Mediterraneans. Hum Mol Genet 6, 1605-1609). This mutation has a carrier frequency of 1.7% in Austria for example, where homozygous 35delG is associated with up to 75% of cases of NSHI (Frei et al., 2005, GJB2 mutations in hearing impairment: identification of a broad clinical spectrum for improved genetic counseling. Laryngoscope 115, 461-465).

SUMMARY OF THE INVENTION

In a first embodiment there is provided a method of identifying a subject at risk for developing non-syndromic hearing impairment (NSHI) comprising detecting a first polymorphism in gap junction beta 2 (GJB2) gene of chromosome 13 at position −228, said position located in a promoter region of GJB2, wherein a subject having a heterozygous or homozygous genotype for a T-228C polymorphism is at increased risk for NSHI compared to a subject with no T-228C polymorphism. Related embodiments provide a method as describe, wherein the first polymorphism is heterozygous genotype −228T/C or homozygous genotype −228CC. Still other related embodiments provide a method as described, further comprising detecting a second polymorphism in the GJB2 gene in recessive locus DFNB1 of chromosome 13, wherein a subject having a heterozygous or homozygous genotype for the T-228C polymorphism and a heterozygous genotype for the second polymorphism is at increased risk for NSHI compared to a subject with no T-228C polymorphism.

In particular related embodiments, the second polymorphism is selected from the group consisting of 35delG, G154C/V52L, C249G/F83L, G262T/A88S, T269C/L90P, G380A/R127H and G457A/V153I. In still more particular related embodiments, the first polymorphism is heterozygous genotype −228T/C and the second polymorphism is 35delG; or the first polymorphism is homozygous genotype −228CC and the second polymorphism is G457A/V 153I.

Another particular embodiment provides a method as described above, further comprising detecting a third polymorphism in GJB2 of chromosome 13, wherein the third polymorphism has a heterozygous 35delG genotype in GJB2 in recessive locus DFNB1 of chromosome 13. In related embodiments, the subject is a member of a family having at least one member diagnosed with non-syndromic hearing impairment. In other particular related embodiments, the subject is an infant from age zero to 24 months, or is a subject from age 24 months to 95, or from age 95 to 100, or even older, age being unimportant as long as the subject is a suitable subject for being screened for hearing loss. In this case, a suitable subject means a subject with a family member at risk, or deemed to be at risk of hearing loss, and someone sufficiently healthy, as determined by a physician, to endure the necessary diagnostic procedures required to screen for non-syndromic hearing impairment, which typically involves the taking of a blood sample from the subject.

In related embodiments there is provided any of the methods as described above, wherein detecting further comprises obtaining a sample of DNA from a subject, amplifying the GJB2 gene sequence having a transcription start site, retrieving a DNA sequence region proximal to the GJB2 transcription start site, amplifying a region between −427 and IVS1 243 of the GJB2 locus to produce amplified DNA products, and sequencing the amplified DNA products.

In more particular related embodiments, the PCR technology may be any of real time PCR technology, multiplex PCR technology, molecular beacon PCR technology, allele-specific PCR technology, amplification refractory mutation system (ARMS), or restriction fragment length polymorphism analysis.

Another particular embodiment provides a nucleotide sequence that hybridizes to a T-228C polymorphism in the promoter region of gap junction beta 2 (GJB2) gene in recessive locus DFNB1 of chromosome 13 under standard or stringent conditions, the nucleotide sequence comprising a subsequence selected from the group consisting of SEQ ID NO: 69, SEQ ID NO: 70, SEQ ID NO: 71, SEQ ID NO: 72, SEQ ID NO: 73, SEQ ID NO: 74, sequences with sufficient sequence identity to SEQ ID NOs: 69-74 to permit them to hybridize to said T-228C polymorphism under standard or stringent conditions, and sequences that are complementary to said sequences.

Still another particular embodiment provides a nucleotide sequence that hybridizes to a T-228C polymorphism in the promoter region of gap junction beta 2 (GJB2) gene in recessive locus DFNB1 of chromosome 13 under standard or stringent conditions, the nucleotide sequence comprising a subsequence selected from the group consisting of SEQ ID NO: 11, SEQ ID NO: 12, SEQ ID NO: 15, SEQ ID NO: 16, SEQ ID NO: 19, SEQ ID NO: 20, SEQ ID NO: 23, SEQ ID NO: 24, SEQ ID NO: 27, SEQ ID NO: 28, SEQ ID NO: 37, SEQ ID NO: 38, SEQ ID NO: 47, SEQ ID NO: 48, sequences with sufficient sequence identity to SEQ ID NOs: 11-12, 15-16, 19-20, 23-24, 27-28, 37-38, 47-48 to permit them to hybridize to said T-228C polymorphism under standard or stringent conditions, and sequences that are complementary to said sequences.

The nucleic acid probe molecules described herein can be used to detect mutations in the regulatory region and in gene expression products such as mRNA. The nucleic acid molecules can be used as hybridization probes to detect naturally occurring genetic mutations in the regulatory region of gap junction beta 2 (GJB2) gene of chromosome 13 and thereby to determine whether a subject with the mutation is at risk for non-syndromic hearing impairment caused by the mutation. Detection of a mutated form of the gap junction beta 2 (GJB2) gene of chromosome 13 provides a diagnostic tool for identifying subjects with non-syndromic hearing loss, or those who are carriers of the mutated form of the gap junction beta 2 (GJB2) gene of chromosome 13 associated non-syndromic hearing loss, or those at risk for developing non-syndromic hearing loss.

Individuals carrying a mutation at position −228 in the gap junction beta 2 (GJB2) gene of chromosome 13 can be detected at the nucleic acid level by a variety of techniques. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202, incorporated by reference herein), such as anchor PCR or RACE PCR, or, alternatively, in a ligation chain reaction (LCR) (see, e.g., Landegran et al., Science 241:1077-1080 (1988), incorporated by reference herein; and Nakazawa et al., PNAS 91:360-364 (1994), incorporated by reference herein), the latter of which can be particularly useful for detecting point mutations in the gene (see Abravaya et al., Nucleic Acids Res. 23:675-682 (1995), incorporated by reference herein). This method can include the steps of collecting a sample of cells from a patient, isolating nucleic acid (e.g., genomic, mRNA or both) from the cells of the sample, contacting the nucleic acid sample with one or more primers and probes which specifically hybridize to the −228 position of gap junction beta 2 (GJB2) gene of chromosome 13 under conditions such that hybridization and amplification of the gene occurs, and sequencing the amplified product compared to a control sample. In this way, point mutations such as the T-228C transition can be identified.

Alternatively, mutations in gap junction beta 2 (GJB2) gene of chromosome 13 can be directly identified, for example, by alterations in restriction enzyme digestion patterns determined by gel electrophoresis.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
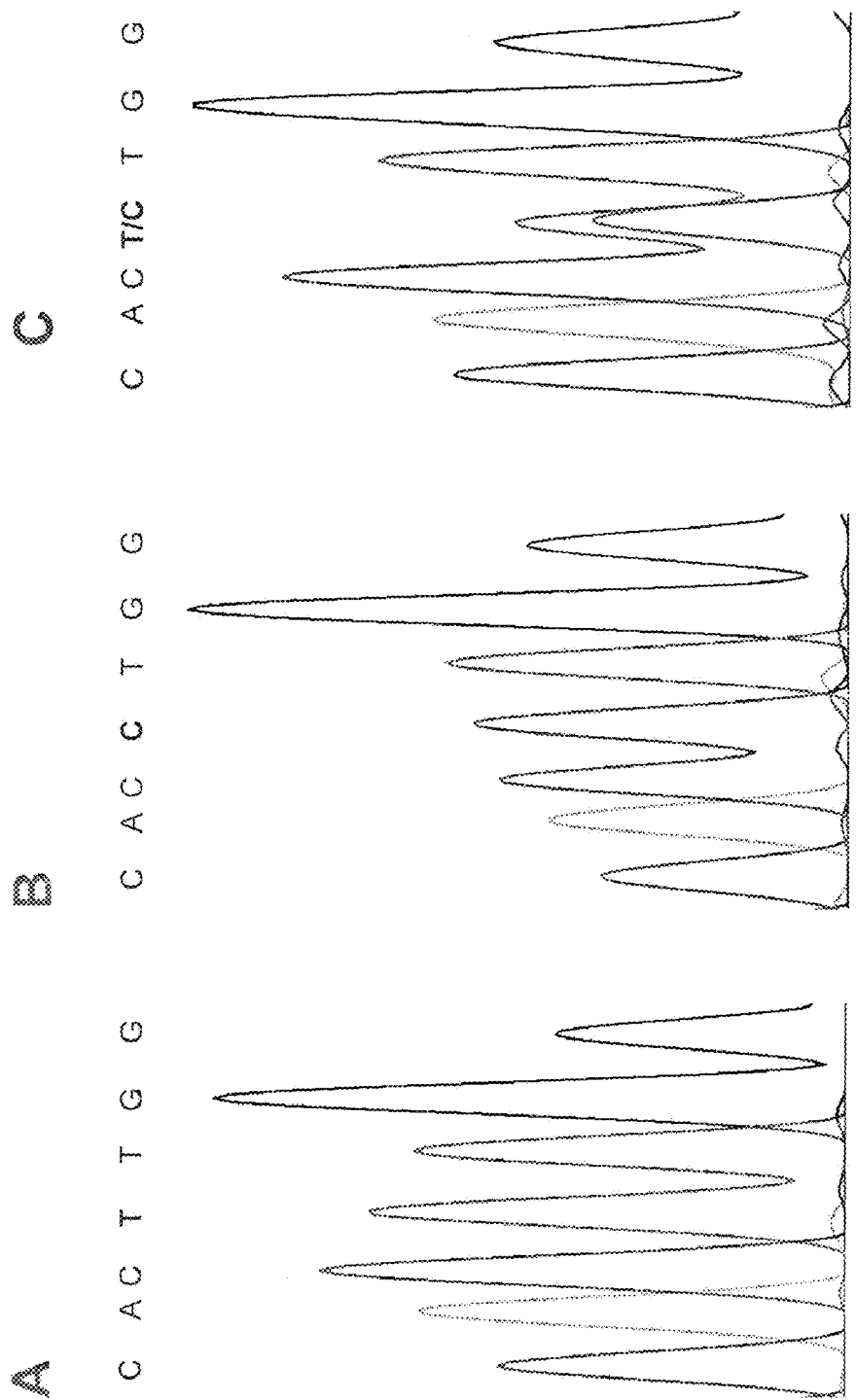
FIG. 1. Depicts sequence traces showing the T/T (A), C/C (B) and T/C (C) homozygous and heterozygous polymorphic variants within the GJB2 promoter at position −228.

As mentioned previously, the most frequent GJB2 mutation in Caucasian populations is the frameshift deletion of a guanine residue at position 35 of the normal coding sequence (35delG) which leads to the introduction of a premature stop codon after base pairs 37-39 (Zelante et al., 1997, Connexin26 mutations associated with the most common form of non-syndromic neurosensory autosomal recessive deafness (DFNB1) in Mediterraneans. Hum Mol Genet 6, 1605-1609). This mutation has a carrier frequency of 1.7% in Austria for example, where homozygous 35delG is associated with up to 75% of cases of NSHI (Frei et al., 2005, GJB2 mutations in hearing impairment: identification of a broad clinical spectrum for improved genetic counseling. Laryngoscope 115, 461-465).

In addition to mutations in the coding region of GJB2, alterations in the potential transcriptional regulatory region of GJB2 have been identified. The GJB2 gene has a 128 bp basal promoter (Tu and Kiang, 1998, Mapping and characterization of the basal promoter of the human connexin26 gene. Biochim Biophys Acta 1443, 169-181) incorporating a TATA box (consensus TTAAAA) at −19 to −24 and 2 GC boxes (consensus CCGCCC) at −76 to −81 and −88 to −93 proximal to the transcriptional start site. The 35delG alteration is considered to have arisen from a common founder chromosome (Van Laer et al., 2001, A common founder for the 35delG GJB2 gene mutation in connexin 26 hearing impairment. J Med Genet 38, 515-518) and is irrevocably associated with a T→C transition 228 bp (T-228C) proximal to the transcriptional start site in homozygous cases of NSHI (Rothrock et al., 2003, Connexin 26 35delG does not represent a mutational hotspot. Hum Genet 113, 18-23).

In approximately 50% of genetic NSHI cases, no known mutations in DFNB1 can be identified and are considered idiopathic. In addition, although the carrier frequencies of combined pathogenic, recessive GJB2 mutations are below 2% in the normal hearing Austrian population, the heterozygous occurrence of 35delG within NSHI groups is over 11% in the Austrian patient collective (Frei et al., 2005, GJB2 mutations in hearing impairment: identification of a broad clinical spectrum for improved genetic counseling. Laryngoscope 115, 461-465). Although we cannot be sure that NSHI is caused by DFNB1 in these patient groups, we reasoned that these patients may contain further novel alterations affecting the cochlear gap junction network within DFNB1 and screened both these patients and NSHI patients with no known mutations in GJB2 for alterations in downstream regulatory sequences.

Homozygous alterations in the gap junction protein GJB2 (connexin 26), within the DFNB1 locus, are responsible for up to 50% of autosomal recessive non-syndromic hearing impairment (NSHI). Mutations have been described throughout the coding region and more rarely, within the splice donor site. To further investigate the role of GJB2 in NSHI, we have now screened the putative 5' regulatory region for novel alterations. In idiopathic cases of NSHI lacking known pathogenic alterations in GJB2, we have now identified a T→C transition 228 bp proximal to the transcriptional start site (T-228C) present at a homozygous frequency of 0.2, which is significantly overrepresented in comparison to the predicted homozygous allele frequencies in the healthy population (0.0144). In a NSHI family, inheritance of T-228C was shown to segregate on independent chromosomes with HI in conjunction with heterozygous inheritance of 35delG, the most common Caucasian mutation in the GJB2 coding region. In a patient group bearing heterozygous pathogenic mutations, homozygosity for T-228C was also highly overrepresented (0.267) and not exclusively linked to the 35delG mutation in cis. However, in all cases of NSHI examined, 35delG homozygousity was linked to T-228C in cis. Bioinformatic analysis of the GJB2 promoter revealed the potential importance of T-228C in the regulation of GJB2 expression. Of regulatory factors known to be expressed in the inner ear, the T-228C transition would delete potential binding sites for the X-box binding protein (RFX1) and the H6 homeobox 3 (HMX3/Nkx5.1) transcription factor which has been linked to hearing impairment. These results suggest that T-228C may represent the most common mutation associated with development of NSHI in Caucasian populations identified to date and should be included in worldwide newborn screening programs for NSHI.

Definitions. As used in this description and the accompanying claims, the following terms shall have the meanings indicated, unless the context otherwise requires:

"Genetic marker" or "marker" as used herein refers to a variable or polymorphic nucleotide sequence that is present in genomic DNA, and which is identifiable with specific oligonucleotides (e.g. distinguishable by nucleic acid amplification and observance of a difference in size or sequence of nucleotides due to the polymorphisma). The "locus" of a genetic marker or markers refers to its place on the chromosome in relation to another locus. Markers, as illustrated herein, can be identified by any one of several techniques known to those skilled in the art, including microsatellite or short tandem repeat (STR) amplification, analyses of restriction fragment length polymorphisms (RFLP), single nucleotide polymorphism (SNP), detection of deletion of insertion sites, and random amplified polymorphs DNA (RAPD) analysis.

"Polymorphism" as used herein refers to a marker that is distinguishably different (e.g. in size, electrophoretic migration, nucleotide sequence, ability to specifically hybridize to an oligonucleotide under standard conditions) as compared to an analogous region from a subject within the same family (e.g. within the family tree).

"Hybridization" as used herein refers to a sufficient number of complementary base pairs in its sequence to interact specifically (hybridize) with the target nucleic acid sequence to be amplified or detected. As known to those skilled in the art, a very high degree of complementarity is needed for specificity and sensitivity involving hybridization, although it need not be 100%. Thus, for example, an oligonucleotide which is identical in nucleotide sequence to an oligonucleotide disclosed herein, except for a few base changes or substitutions, may function equivalently to the disclosed oligonucleotides.

"Hybridization Under Standard conditions" as used describes those conditions under which substantially complementary nucleic acid segments will form standard Watson-Crick base-pairing. A number of factors are known that determine the specificity of binding or hybridization, such as pH, temperature, salt concentration, the presence of agents, such as formamide and dimethyl sulfoxide, the length of the segments that are hybridizing, and the like. Standard hybridization conditions include conditions under which nucleic acid molecules are used to identify similar nucleic acid molecules. Such standard conditions are disclosed, for example, in Sambrook et al., Molecular Cloning: A Laboratory Manual, Cold Spring Harbor Labs Press, 1989. Sambrook et al., ibid., is incorporated by reference herein in its entirety (see particularly, pages 9.31-9.62 and 11.45-11.61).

Hybridization conditions vary according to the level of stringency desired The temperature and salt concentrations at which hybridization is performed has a direct effect upon the results that are obtained. Specifically, the hybridization conditions can be designed so that hybridizations occur between the probe and a filter bound nucleic acid that is highly homologous to that probe. Conditions can also be designed wherein the hybridization occurs with a nucleic acid that has a lower degree of homology to the probe.

Hybridization results are directly related to the number of degrees below the Tm of DNA at which the experiment is performed. Under typical salt-containing hybridization conditions, the effective Tm is what controls the degree of homology between the probe and the target DNA, and is required for successful hybridization. The formula for the Effective Tm (Eff Tm) is:

$$\text{Eff Tm} = 81.5 + 16.6(\log M[Na+]) + 0.41(\% G+C) - 0.72(\% \text{ formamide})$$

One salt solution typically used in hybridization experiments is SSC (standard sodium citrate), but NaCl can also be used. In hybridization, a 1% mismatch of two DNAs lowers the Tm 1.4° C. In general, hybridization experiments with oligonucleotide probes are often performed at Tm −20° C. The wash step in hybridization experiments may involve first a non-stringent wash to remove the non-specifically bound DNA and then a second wash at a higher stringency that only permits highly homologous sequences to remain bound to the target DNA. Controlling the stringency is an important step. In general, the final wash is the one of concern when determining the relatedness of the probe and the target nucleic acid. In general, the percent homology is directly related to the most stringent condition in the hybridization experiment, which is typically the final wash.

Formulae to calculate the appropriate hybridization and wash conditions to achieve hybridization permitting varying degrees of mismatch of nucleotides are disclosed, for example, in Meinkoth et al., 1984, Anal. Biochem. 138, 267-284, incorporated by reference herein in its entirety.

"Hybridization Under Stringent Conditions" as used describes those conditions under which nucleic acid molecules, preferably DNA molecules, hybridize to, and are therefore the complements of, the DNA target sequences of interest believed to contain a mutation at, among other places, −228 in the regulatory region of GJB2. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for ~14-base oligos), 48° C. (for ~17-base oligos), 55° C. (for ~20-base oligos), and 60° C. (for ~23-base or higher oligos). These nucleic acid molecules may be used as components of diagnostic methods whereby the presence of a hearing loss-causing allele or polymorphism, may be detected.

Another example of stringent hybridization conditions includes hybridization in which the target sequences (or a portion thereof) are identified using oligonucleotide probes detectably labeled and suspended in a hybridization buffer consisting essentially of 50% formamide, 5× sodium chloride/sodium phosphate/EDTA (SSPE; 1×SSPE is 0.15 mM NaCl, 1 mM NA-EDTA, 10 mM Na-phosphate (pH 7.0), 5×Denhardt's solution (0.1% polyvinylpyrrolidone, 0.1% Ficoll)). The hybridization buffer is contacted with the target DNA sequence (or portion there) at about 45° C. for a period of several hours. The hybridization solution is then removed, and non specifically bound nucleic acid is removed by repeated washing with 1×SSC at increasing temperatures (up to 65° C.).

As used herein, the term "hybridization under stringent conditions also describes conditions for hybridization and washing under which nucleotide sequences complementary to the regulatory region having the possible T-228C transition are at least 60-70% homologous to each other and typically remain hybridized to each other. The conditions can be such that sequences at least about 60%, at least about 70%, or at least about 80% or at least about 90% or more homologous to each other typically remain hybridized to each other. As described, such stringent conditions are known to those skilled in the art and can also be found in Current Protocols in Molecular Biology, John Wiley & Sons, N.Y. (1989), 6.3.1-6.3.6. Another example of stringent hybridization conditions are hybridization in 6× sodium chloride/sodium citrate (SSC) at about 45° C., followed by one or more washes in 0.2×SSC, 0.1% SDS at 50-65° C. Examples of moderate to low stringency hybridization conditions are also well known in the art and have been described.

Methods for determining how to calculate and identify stringent conditions for oligonucleotide probes and a target sequence are disclosed, for example, in Sambrook et al., Molecular Cloning: A Laboratory Manual, Cold Spring Harbor Labs Press, 1989 (see particularly, pages 11.45-11.47). In addition, as described above, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284.

As used here, a "genetic subset" of a population consists of those members of the population having a particular genotype. In the case of a biallelic polymorphism, a population con potentially be divided into three subsets: homozygous for allele 1 (1,1), heterozygous (1,2), and homozygous for allele 2 (2,2). A 'population' of subjects may be defined using various criteria, e.g., individuals diagnosed with a certain medical condition, such as NSHI, individuals of a defined ethnicity, individuals of the same sex, or individuals from a certain demographic group, etc.

As used herein, a subject that is "predisposed to" or "at increased risk of developing" a particular phenotypic response based on genotyping will be more likely to display that phenotype than an individual with a different genotype at the target polymorphic locus (or loci).

"Genetic testing", also referred to as "genetic screening" as used herein refers to the testing of a biological sample from a subject to determine the subject's genotype: and may be used to determine if the subject's genotype comprises alleles that either cause, or increase susceptibility to, a particular phenotype, or that are in linkage disequilibrium—i.e. occur at a frequency greater than statistically predicted—with allele(s) causing or increasing susceptibility to that phenotype.

"Linkage equilibrium" can be thought of as the two locus version of the Hardy-Weinberg ratio, but it is a property of haplotypes, not genotypes. A diploid individual has two haplotypes, and at the equilibrium the genotypes at each locus will be in Hardy-Weinberg proportions while the haplotypes are at linkage equilibrium. Like the Hardy-Weinberg ratio, it is an equilibrium because in the absence of selection and with random mating the action of recombination over time will drive the haplotypes to random frequencies and then keep them there.

In the present case, in a patient group bearing heterozygous pathogenic mutations, homozygousity for T-228C was highly overrepresented (0.267) and not exclusively linked to the 35delG mutation in cis. However, in all cases of NSHI examined, 35delG homozygousity was linked to T-228C in cis.

"Linkage disequilibrium" refers to the tendency of specific alleles at different genomic locations to occur together more frequently than would be expected or predicted by natural, random chance. Alleles at a given loci are in complete equilibrium if the frequency of any particular set of alleles (or haplotypes) is the product of their individual population frequencies.

$$\text{A commonly used measure of linkage disequilibrium is } r^2 \text{ (or } \Delta^2\text{)} = \frac{D_{AB}^2}{P_A(1-P_A)P_B(1-P_B)} = \frac{\chi^2}{2n}.$$

The linkage disequilibrium expression $r^2$ ranges from between 0 and 1. The value of r2 is 1 when the two markers provide identical information. The value of $r^2$ is 0 when the two markers are in perfect equilibrium. The expected value is ½.

Alternatively, a normalized measure of linkage disequilibrium can be defined as:

$$D' = \frac{D_{AB}}{\min(P_A P_B P_a P_b)}$$
$$\frac{D_{AB}}{\min(P_A P_b P_a P_B)}.$$

The value of the D' has a range of −1.0 to 1.0. When statistically significant absolute D' value for two markers is not less than 0.3 they are considered to be in linkage disequilibrium.

Materials and Methods

Patients

Individuals were recruited from the Department of Otorhinolaryngology, University hospital of Vienna. Informed consent was obtained from all individuals or the parents of minors and the study was approved by the University of Vienna ethics commission. Complete medical histories, otolaryngological status and audiometrical analysis of all individuals were examined. In several cases, otoacoustic emissions, brainstem evoked response audiometry, ophthalmic evaluations, computer tomography and magnetic resonance imaging of temporal bone and blood analyses were performed to ascertain disease status. Syndromic forms and patients with temporal bone anomalies or suspected exogenetic causes of NSHI were identified from medical histories and not included into the study. NSHI patients included in the study group (n=15) were non-related carriers of a single pathogenic coding mutation in GJB2. NSHI familial cases of deafness were identified when at least two affected individuals had a first degree relationship. Allele frequencies within the Austrian population were determined in normal hearing control subjects (n=50).

Sample Composition and Clinical Evaluation for Screening for Subjects at Risk for NSHI Infants from families or subsets of populations may be studied or screened to identify those at risk to develop NSHI. One selection criterion for identifying the infants to be screened from a population subset comprises identifying infants from families with at least one member with HI. Alternatively, a subset of infants from the general population may be identified and screened, wherein the subset includes infants from a particular ethnic group, those of a particular sex, infants from a particular demographic group, or the like. In addition, a subset of the population of infants may be identified and screened, wherein the population subset comprises infants whose parent volunteers them to be tested, infants who are recommended to be tested, or infants who simply are tested for any of a variety of reasons. All subjects are evaluated using standard protocols.

In addition to the family samples, a matched subset case control collection is also evaluated (such as 20 cases and 20 controls, 50 cases and 50 controls, for example). A primary diagnostic criteria for a given collection could be a definite physician's diagnosis for the presence or absence of 35delG in the GJB2 gene on DFNB1 locus of chromosome 13, or a definitive physician's diagnosis of hearing impairment with no known reason.

DNA Isolation, PCR and Bioinformatics

DNA was extracted from peripheral blood by salt extraction. The full coding sequence of GJB2 was amplified and sequenced as described previously (Frei et al., 2002, Connexin 26 mutations in cases of sensorineural deafness in eastern Austria. Eur J Hum Genet 10, 427-432). The sequence region proximal to the GJB2 (GenBank accession NM_004004) transcription start site was retrieved from the build 36.2 chromosome 13 genomic contig (NT_024524.13) and the region between −427 and IVS1 243 of the GJB2 locus amplified with forward 5'-CGCACTATGCGGAGTACAGA-3' (SEQ ID NO: 1) and reverse 5'-GGTGGCAGTGGGT-CAAGTAG-3' (SEQ ID NO: 2) primers in a reaction mixture containing 200 µM dNTPs, 2 mM MgCl$_2$, 20 mM Tris-HCl (pH 8), 50 mM KCl, 5% DMSO and 1U Platinum Taq polymerase (Invitrogen, Carlsbad, Calif.) for 40 cycles of amplification with annealing at 58° C. for 40 sec, extension at 72° C. for 60 sec, denaturation at 94° C. for 40 sec and end extension at 72° C. for 7 min in a GeneAmp® PCR System 9700 thermal cycler (PE Applied Biosystems, Foster City, Calif.). PCR products were separated on 1.5% agarose gels containing 0.5 µg/ml ethidium bromide at 1 V/cm, sequenced on an ABI sequencer and results compared to the wild type locus sequence using the ncbi interface (http://www.ncbi.nlm.nih.gov/blast/b12seq/b12.html). Transcription factor binding sites were identified by literature searches.

Statistical Analysis

Statistical significance (departure from the Hardy-Weinberg equilibrium) between groups was assessed with the Chi-square test by testing the difference between the expected (calculated from the allelic frequencies) and observed genotype frequencies. A value of p<0.05 was considered significant.

Results and Discussion

Amplification of GJB2

To identify potential genetic alterations within the GJB2 regulatory region that may play a role in NSHI, we initially amplified and sequenced the region between −427 and IVS1 243 to examine 407 bp of proximal regulatory sequence in the normal healthy Austrian population (n=50), in NSHI patients bearing no known mutations in DFNB1 (n=10) and in a NSHI patient group (n=15) bearing a single, heterozygous, pathogenic coding mutation in GJB2. Mutations included in the patient group were 35delG (Denoyelle et al., 1999, Clinical features of the prevalent form of childhood deafness, DFNB1, due to a connexin-26 gene defect: implications for genetic counselling. Lancet 353, 1298-1303), G154C/V52L (Frei et al., 2005, GJB2 mutations in hearing impairment: identification of a broad clinical spectrum for improved genetic counseling. Laryngoscope 115, 461-465), C249G/F83L (Scott et al., 1998, Identification of mutations in the connexin 26 gene that cause autosomal recessive nonsyndromic hearing loss. Hum Mutat 11, 387-394), G262T/A88S (Frei et al., 2002, Connexin 26 mutations in cases of sensorineural deafness in eastern Austria. Eur J Hum Genet 10, 427-432), T269C/L90P (Murgia et al., 1999, Cx26 deafness: mutation analysis and clinical variability. J Med Genet 36, 829-832), G380A/R127H (Estivill et al., 1998, Connexin-26 mutations in sporadic and inherited sensorineural deafness. Lancet 351, 394-398) and G457A/V153I (Frei et al., 2002, Connexin 26 mutations in cases of sensorineural deafness in eastern Austria. Eur J Hum Genet 10, 427-432). Other known changes that can lead to NSHI within DFNB1 such as GJB6-D13S1830 and GJB6-D13S1854 were previously excluded from the study group. Within the amplified sequence, the GJB2 IVS1+1G>A (also known as—G3170A) exon 1 splice site mutation (Denoyelle et al., 1999, Clinical features of the prevalent form of childhood deafness, DFNB1, due to a connexin-26 gene defect: implications for genetic counselling. Lancet 353, 1298-1303; Seeman and Sakmaryova, 2006, High prevalence of the IVS 1+1 G to A/GJB2 mutation among Czech hearing impaired patients with monoallelic mutation in the coding region of GJB2. Clin Genet 69, 410-413) was excluded as a cause of NSHI by sequence analysis.

Allele Frequencies of GJB2 T-228C in the Healthy Population

The T-228C transition was identified within the GJB2 regulatory region in the healthy Austrian population and the patient group by direct sequencing (FIG. 1). In the healthy population (n=50), the genotype frequencies were identified as 74% for −228TT and 26% for −228TC (Table 1) which are comparable with frequencies described previously (Rothrock et al., 2003, Connexin 26 35delG does not represent a mutational hotspot. Hum Genet 113, 18-23) as SNP1245. Although no examples of the CC genotype were found, if the genotype frequencies were to follow a Hardy-Weinberg equilibrium with the calculated frequency of T (p=0.87) and C (q=0.13) within the group, the expected frequency of CC ($q^2$) of 0.0144 would predict this genotype appearing only 0.845 times in a sample of 50.

According to the Hardy-Weinberg equilibrium, the frequency of a given allele can be expressed as an algebraic expression using the expansion of the binomial $(p+q)^2$. $(p+q)^2 = p^2 + 2pq + q^2$. The total number of genes in a population is its gene pool. Within that gene pool, p represents the frequency of a given gene in the pool and q the frequency of its single allele. Therefore, p+q=1, $p^2$ defines the fraction of the population homozygous for p, $q^2$ defines the fraction homozygous for q and 2pq defines the fraction of the population that is heterozygous. In this case, the measured allelic frequency of the T-228C polymorphism in the promoter region of the GJB2 gene for the DFNB1 recessive locus of chromosome 13 does not follow the expected Hardy-Weinberg equilibrium prediction for the allelic frequency of the T-228C polymorphism within this locus.

TABLE 1

| Group (number) | GJB2 genotype (-228) Number (frequency) | | |
|---|---|---|---|
| | T/T | C/T | C/C |
| Healthy (50) | 37 (0.74) | 13 (0.26) | 0 |
| GJB2 heterozygous (15) | 7 (0.466) | 4 (0.267) | 4 (0.267) |

Table 1. Genotyping of the GJB2 promoter at position −228 in healthy control subjects (n=50) and a non-syndromic hearing loss patient group bearing a single, pathogenic heterozygous mutation in the GJB2 coding sequence (n=15).

Association of T-228C with Non-DFNB1 Associated NSHI

In a NSHI patient group (n=10) bearing no previously identified mutations in GJB2, in which the genetic causes of NSHI were unknown, monogenetic carriage of −228CC is associated with HL (Table 2). In comparison to the predicted frequency of −228CC in the healthy population (1.44%), −228CC was found in 2/10 cases (20%) suffering from severe and profound NSHI.

TABLE 2

| Group | Severity of NSHI |
|---|---|
| -228TT | mo (3), se (1), pr (3) |
| -228CT | se (1) |
| -228CC | se (1), pr (1) |

Table 2. Genotypes at position −228 of the GJB2 promoter of non-syndromic hearing loss patients with wild type GJB2 (n=10). The degree of bilateral HL (phenotype) was defined as moderate 40-55 dB (mo), severe 55-70 dB (se) or profound 70-90 dB (pr).

Association of T-228C with Heterozygous GJB2 Pathogenic Mutations

As shown in Table 3, a significant difference in allele frequencies was found between the healthy population and the patient group. In contrast to the healthy population (predicted CC frequency 0.0144), 4 examples of −228CC were found in the group of 15 (frequency 0.267) representing an 18.5 fold increase. A corresponding 37% decrease in −228TT frequency was accompanied by only a 2.7% increase in −228TC frequency (statistical significance between the allelic groups p<0.005).

No Founder Effect for 35delG

The most common pathogenic GJB2 mutation in Austria is 35delG (Frei et al., 2002, Connexin 26 mutations in cases of sensorineural deafness in eastern Austria. Eur J Hum Genet 10, 427-432) which is correspondingly overrepresented (n=8/15) in the patient group. Evidence has been provided previously that 35delG is derived from a common ancient founder (Van Laer et al., 2001, A common founder for the 35delG GJB2 gene mutation in connexin 26 hearing impairment. J Med Genet 38, 515-518) and in the original work describing the T-228C polymorphism, −228C/C was found to be irrevocably linked to inheritance of homozygous 35delG in different hearing impaired populations worldwide (Rothrock et al., 2003, Connexin 26 35delG does not represent a mutational hotspot. Hum Genet 113, 18-23). A comparable linkage phenomenon had also been reported with the GJB2 T101C (M34T) alteration which is associated on 88% of alleles with a deletion of 10 base pairs (−493del 10) in the regulatory region (Houseman et al., 2001, Genetic analysis of the connexin-26 M34T variant: identification of genotype M34T/M34T segregating with mild-moderate non-syndromic sensorineural hearing loss. J Med Genet 38, 20-25). Similarly, when we determined the promoter genotype in an Austrian homozygous 35delG NSHI group (n=10), homozygous −228CC was found in all cases.

TABLE 3

| Heterozygous GJB2 mutation | Severity of NSHI |
|---|---|
| -228TT | |
| 35delG (frameshift) | mo (2), pr (1) |
| G154C (V52L) | mi/mo (1) |
| C249G (F83L) | pr (1) |
| G262T (A88S) | pr (1) |
| T269C (L90P) | mo (1) |
| -228CT | |
| 35delG | mi (2), pr (1) |
| G380A (R127H) | pr |
| -228CC | |
| 35delG | mo (1), pr (2) |
| G457A (V153I) | pr (1) |

Table 3. Genotypes at position −228 of the GJB2 promoter of non-syndromic hearing loss patients bearing a single pathogenic heterozygous mutation in the GJB2 coding sequence (n=15). The degree of bilateral HL (phenotype) was defined as mild 20-40 dB (mi), moderate 40-55 dB (mo), severe 55-70 dB (se) or profound 70-90 dB (pr).

In the heterozygous NSHI patient group, however, the 35delG frameshift was associated with all −228 genotypes and with mild, moderate and profound NSHI (Table 3). These data show that in a patient group where GJB2 heterozygousity is only presumed to be linked to NSHI and should consequently contain cases of non-GJB2 caused NSHI, 35delG is not always associated with T-228C. The implications of these findings are that the founder 35delG arose independently of the nucleotide at −228 and that T-228C may be directly linked to the development of NSHI.

Occurrence of T-228C in Heterozygous GJB2 Associated NSHI

The −228CC genotype was associated with heterozygous G457A/V153I (n=1) and 35delG (n=3) in the patient group. Subdivision of the complete patient group (n=15) into non-35delG carriers (n=6) would implicate the occurrence of −228CC in 16.7% of cases compared to the predicted 1.44% −228CC frequency in the healthy population again linking −228CC with NSHI.

Segregation of T-228C with NSHI

Figure 2:
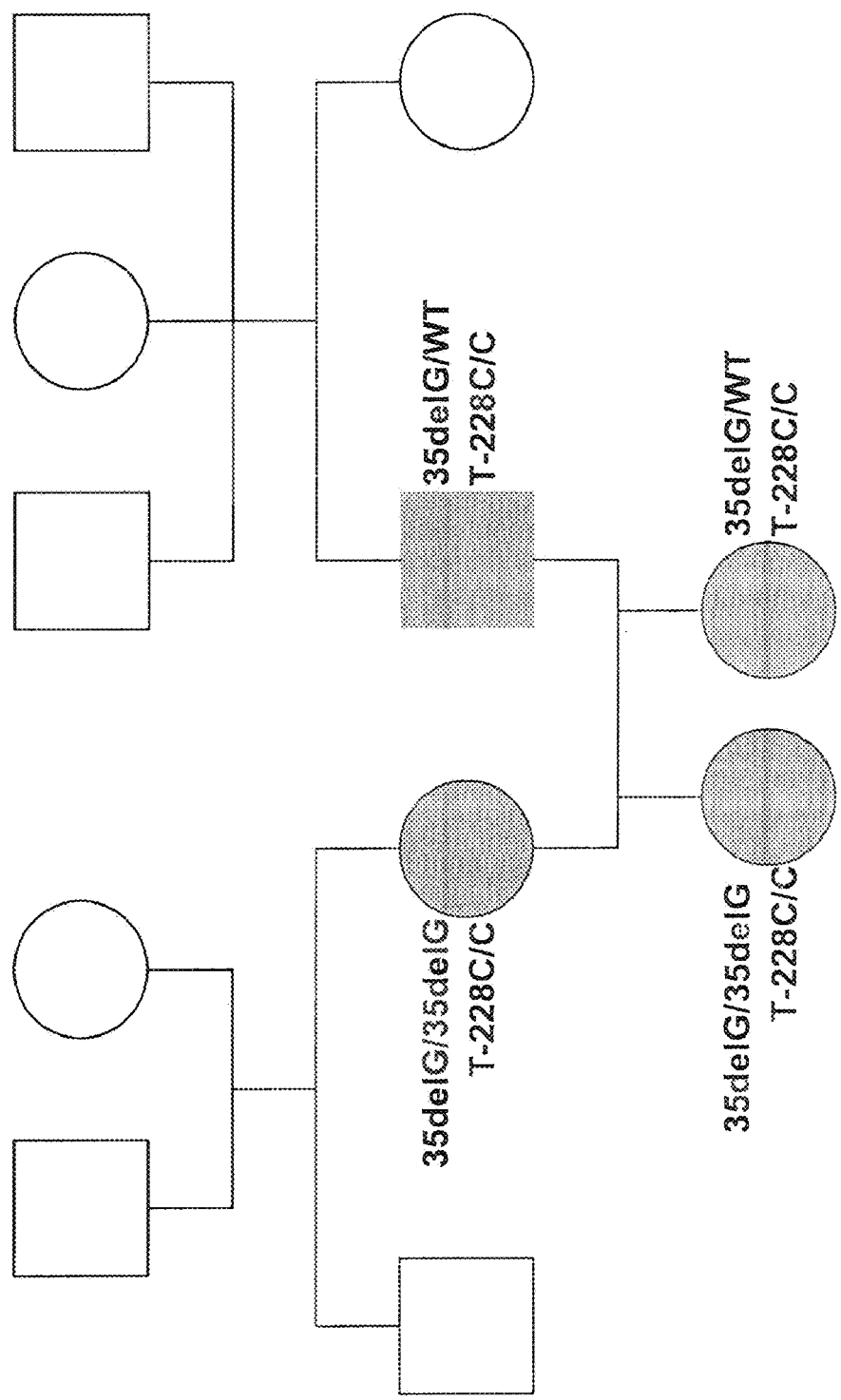
FIG. 2. Shows segregation of GJB2 T-228C and 35delG within an autosomal recessive NSHI family. Inheritance of −228C in cis with wild type GJB2 is associated with development of NSHI in the mother (pro) and daughter (pro).

Since −228CC may therefore lead to HI, we then examined a NSHI family in which 35delG heterozygousity of the father and one of the daughters had previously prevented the genetic diagnosis of GJB2 caused HI. In this case, the inheritance of T-228C was shown to segregate on independent chromosomes with HI in conjunction with heterozygous inheritance of 35delG, the most common Caucasian mutation in the GJB2 coding region. As shown in FIG. 2, T-228C inheritance in cis with wild type GJB2 is associated with NSHI and segregates both dependently and independently of 35delG within the family.

Transcription Factor Binding Potentials Altered by T-228C

Since monogenetic T-228C is linked to the development of NSHI, we then analyzed the potential relevance of the T-228C transition by transcription factor (TF) binding site analysis of the GJB2 regulatory region (Table 4). The T-228C variant potentially creates binding sites for AREB6, the Lim Domain only 2 (LMO2) TF (also known as rhombotin-2, rhombotin-like 1 and T-cell translocation gene 2) complex and heterodimers of the bHLH transcription factors HAND2 (Thing2) and E12. The Atp1a1 regulatory element binding factor AREB6 (also known as TCF-8, deltaEF-1, Nil-2a, ZEB1, ZFHEP and Zfxh1A) is known to regulate genes such as the α subunit of the $Na^+/K^+$ATPase (Watanabe et al., 1993, Transcription factors positively and negatively regulating the Na,K-ATPase alpha 1 subunit gene. J Biochem (Tokyo) 114, 849-855) and collagen type IV alpha 3 (COL4A3) for example (Krafchak et al., 2005, Mutations in TCF8 cause posterior polymorphous corneal dystrophy and ectopic expression of COL4A3 by corneal endothelial cells. Am J Hum Genet 77, 694-708), mutations which lead to Alport syndrome which is accompanied by sensorineural hearing loss (Barker et al., 1990, Identification of mutations in the COL4A5 collagen gene in Alport syndrome. Science 248, 1224-1227). T-228C would also negate the binding potentials at this position of h6 homeobox 3 (also known as nkx5.1), the ras-responsive element binding protein 1 (RREB1) and the x-box binding protein (RFX1). HMX3 expression, for example, is essential for development of the inner ear (Wang et al., 2004, Hmx2 and Hmx3 homeobox genes direct development of the murine inner ear and hypothalamus and can be functionally replaced by Drosophila Hmx. Dev Cell 7, 439-453), is expressed in the cochlea only in the stria vascularis and has been linked to HL (Rinkwitz-Brandt et al., 1995, Distinct temporal expression of mouse Nkx-5.1 and Nkx-5.2 homeobox genes during brain and ear development. Mech Dev 52, 371-381). RFX1 is also expressed in the supporting cells of the inner ear and is enriched in hair cell populations (Cristobal et al., 2005, Assessment of differential gene expression in vestibular epithelial cell types using microarray analysis. Brain Res Mol Brain Res 133, 19-36) and brain neurons (Ma et al., 2006, The transcription factor regulatory factor X1 increases the expression of neuronal glutamate transporter type 3. J Biol Chem 281, 21250-21255).

TABLE 4

| Transcription factor | Position |
| --- | --- |
| HMX3/Nkx5.1 | 222-34 |
| RREB1 | 202-16 |
| RFX1 | 222-40 |
| AREB6 | 223-35 |
| Lmo2 complex | 222-36 |
| HAND2 and E12 | 225-39 |

Table 4: Transcription factor binding site analysis of the GJB2 promoter surrounding nucleotide −228 (underlined) relative to the transcription start site. The vertebrate Transfac matrix identities (matrix) identified are shown.

Screening of newborns for GJB2 mutations has become routine worldwide in the diagnosis, prognosis, genetic counselling and therapy of NSHI. An early diagnosis of DFNB1 linked hearing impairment excludes damage to the cochlear nerve and enables the rapid planning of therapeutical intervention such as cochlear implantation. Here we have identified a mutation within the putative regulatory region of GJB2 which is the most common NSHI alteration identified to date in a Caucasian population and will not only considerably expand the scope of genetic counselling for GJB2 alterations but also reduce the time and cost of newborn screening programs.

According to the present methods, a compound may be screened for variation in its effectiveness in treating NSHI among genetic subpopulations of subjects. The phenotypic response of subjects to an NSHI treatment may include the magnitude, duration, or occurrence of a positive response to treatment, or the magnitude, duration or occurrence of an unwanted side effect, or the absence of any response. Methods of correlating genotype with phenotypic response to treatment include administering the therapeutic to a population of subjects, obtaining biological samples from the subjects, genotyping polymorphic allelic sites as identified herein, and correlating the genotype of the subjects with their phenotypic response (e.g., response to therapeutic treatment).

Polymorphic alleles may be detected by determining the DNA polynucleotide sequence, or by detecting the corresponding sequence in RNA transcripts from the polymorphic gene, or where the nucleic acid polymorphism results in a change in an encoded protein by detecting such amino acid sequence changes in encoded proteins; using any suitable technique as is known in the art. Polynucleotides utilized for typing are typically genomic DNA, or a polynucleotide fragment derived from a genomic polynucleotide sequence, such as in a library made using genomic material from the individual (e.g. a cDNA library). The polymorphism may be detected in a method that comprises contacting a polynucleotide or protein sample from an individual with a specific binding agent for the polymorphism and determining whether the agent binds to the polynucleotide or protein, where the binding indicates that the polymorphism is present. The binding agent may also bind to flanking nucleotides on one or both sides of the polymorphism, for example at least 2, 5, 10, 15 or more flanking nucleotide in total or on each side. The polymorphism may also be detected in the double stranded form, but is typically detected in the single stranded form.

In RFLP analysis, −228C specifically creates sites for the restriction enzymes AccB1I, BanI, BshNI and Eco64I which are absent in −228T. Use of these enzymes would permit the homozygous and heterozygous presence of T-228C. In allele specific PCR, the nucleotide at −228 would be selectively amplified in a PCR reaction by incorporating the polymorphic nucleotide into the 3' terminus of the primer. Examples of allele specific primers to detect T-228C would be GCCCCCATGAGTTCCCCA$\underline{N}$-3' (SEQ. ID. NO.:3) and AGCCCCCATGAGTTCCCCA$\underline{N}$-3' (SEQ. ID. NO.: 4), wherein N=A or G.

In other embodiments, the polymerase chain reaction (PCR), such as real-time PCR, may be used to detect the T-228C polymorphism. In real-time PCR, a thermal-stable polymerase is used to amplify DNA sequences flanking and encompassing the DNA sequence of interest which potentially contains the T-228C polymorphism. In this embodiment, fluorescently tagged PCR probes, such as TaqMan® probes, are designed, one to detect the T at position −228, and the other to detect the C on the other chromosome at position −228, along with suitable primers for the Taq polymerase. The probes have a fluorogenic reporter molecule on the 5'-end of the probe, and a quencher molecule on the 3'-end, in close enough proximity to allow the quencher molecule to quench fluorescence. At the commencement of the PCR reaction, the probe and primers are hybridized to the target DNA sequence during the annealing stage, and fluorescence is still quenched. However, once polymerization/amplification of the DNA target sequence begins, the probe is degraded by the 5'→3' exonuclease activity of the Taq polymerase and fluorescence occurs. In such a system, a polymerase having 5'→3' exonuclease activity is required. Using real time PCR, the polymerase amplifies ~100-200 nucleotides adjacent to or flanking the region where the fluorescent probes initially bind. Such techniques are well-known to those of skill in the art, and can be optimized, as needed, for individual situations and polymorphisms of interest. Examples of such reporter/quencher systems and protocols are described in TaqMan Principles for the ABI PRISM® 7700 Sequence Detection System as described at http://www.med.unc.edu/anclinic/Tm.htm as retrieved on Feb. 8, 2008 05:11:24 GMT and downloaded on Feb. 13, 2008, the contents of which are incorporated by reference herein; and described in Applied Biosystem's Protocol for the TaqMan® One-Step RT-PCR Master Mix Reagents Kit, copyright 2006, Applied Biosystems, as described in pp. 1-44 at http://www3.appliedbiosystems.com/cms/groups/mcb_support/documents/generaldocuments/cms_041056.pdf, as downloaded on Feb. 13, 2008, the contents of which are incorporated by reference herein.

Alternatively, a molecular beacon approach may be employed. Homozygous and heterozygous sequences in real-time PCR would be recognized by terminal labeling of discriminatory beacons with a fluorophore and a quencher. An example of molecular beacons to detect A/T base pairing at position –228 would be CCAGCGATGAGTTCCCC AAGTGCCCGCTGG (SEQ. ID. NO.: 5) and to detect C/G base pairing CCAGCGATGAGTTCCCCAGGTGCCCGCTGG (SEQ. ID. NO.: 6) where the discriminatory nucleotide is indicated and the hairpin stem is underlined. Alternatively, in an amplification refractory mutation system (ARMS) analysis involving primer based allele specific extension, the –228 genotype could for example be detected with the discriminatory scorpion primer probes CTCCTAGTTCCTTTGAGCCCGCACTTGGGGAACT-CATGG (SEQ. ID. NO.: 7) and CTCCTAGTTCCTTTGAGCCCGCACCTGGGGAACT-CATGG (SEQ. ID. NO.: 8) (where position –228 is underlined). Suitable primers and probes may be designed using the techniques and instructions available from Glen Research Products for DNA and RNA Synthesis, pp. 1-6, as downloaded on Feb. 13, 2008, at http://www.glenres.com/GlenReports/GR15-11.html, incorporated by reference herein (molecular beacon) and by following the protocols described and referenced by C. Ng, et al., "Multiplex Real-Time Assay Using Scorpion Probes and DNA Capture for Genotype-Specific Detection of Giardia lamblia on Fecal Samples" J. Cin. Microbiol., (2005) vol. 43, pp. 1256-1260, incorporated by reference herein (multiplex PCR using scorpion probes). A useful, though brief, overview of protocols, products and software available to help design various probes for real-time PCR can be found in the Real-Time PCR Guide provided by Premier Biosoft International at http://www.premierbiosoft.com/tech_notes/real_time_PCR.html, as downloaded on Feb. 13, 2008, pp. 1-3, copyright 1994-2008 PREMIER Biosoft International, the contents of which are incorporated by reference herein.

Alternatively, a dye that fluoresces when it binds to dsDNA, may be used to bind to the amplified dsDNA, rather than using probes having a reporter molecule and quencher molecule, as described above. Suitable dyes include SYBR® Green I and SYBR® Green II, YOYO®-1, TOTO®-1, POPO®-3 or any other dye that allows rapid, sensitive detection of amplified target nucleic acid sequence using fluorescence, such as the dyes described in Invitrogen's Molecular Probes bulletin section 8.7, "Analysis of DNA Structure, DNA Binding and DNA Damage, pages 1-7, at http://www-.probes.com/handbook/sections/0807.html, downloaded Feb. 13, 2008, as updated Apr. 5, 2005, copyright 2007, Invitrogen Corporation., the contents of which are incorporated by reference herein. Such techniques are well-known to those skilled in the art, and reaction conditions can be readily optimized to allow amplification of DNA and identification of polymorphisms in a target DNA sequence, including the T-228C polymorphism in the target DNA sequence encompassing the regulatory region of the GJB2 gene.

Using what is known (published) for the sequence corresponding to the –228 area of the regulatory region of GJB2 (see e.g. WO2007009755; EP1308458; and WO2006009870), the general target region may include the following subset sequences (SEQ ID NOs: 9 and 10) of those published sequences, wherein the outlined nucleotide represents the location of the possible polymorphism of interest:

```
SEQ ID NO: 9:
(-340) CGCTTCCTGG GGGGTCCCGA CTCTCAGCCG

CCCCCGCTTC ACCCGGGCCG CCAAGGGGCT GGGGGAGGCG

GCGCTCGGGG TAACCGGGGG AGACTCAGGG CGCTGGGGGC

ACTGGGGAA CTCATGGGGG CTCAAAGGAA CTAGGAGATC

GGGACCTCGA AGGGGACTTG GGGGGTTCGG GGCTTTCGGG

GGCGGTCGGG GGTTCGC (-134)

SEQ ID NO: 10:
(-340) CGCTTCCTGG GGGGTCCCGA CTCTCAGCCG

CCCCCGCTTC ACCCGGGCCG CCAAGGGGCT GGGGGAGGCG

GCGCTCGGGG TAACCGGGGG AGACTCAGGG CGCTGGGGGC

ACCTGGGGAA CTCATGGGGG CTCAAAGGAA CTAGGAGATC

GGGACCTCGA AGGGGACTTG GGGGGTTCGG GGCTTTCGGG

GGCGGTCGGG GGTTCGC (-134)
```

Based on the published sequence of the regulatory region of GJB2 described in e.g. WO2007009755; EP1308458; and WO2006009870, primers and probes can be designed to identify the T-228C polymorphism in samples from subjects. Exemplary primer/probe sets include the following sequences (SEQ ID NOs: 11-66) wherein fluorescent reporter molecules and quenchers are indicated by the * and #, respectively, on each probe:

```
SEQ ID NO: 11: *GGCACTTGGGGAACTC# (probe 1T)

SEQ ID NO: 12: *GGCACCTGGGGAACTC# (probe 1C)

SEQ ID NO: 13: GGGTCCCGACTCTC (primer 1)

SEQ ID NO: 14: TCCTAGTTCCTTTGAGC (primer 1')

SEQ ID NO: 15: *CTGGGGGCACTTGGGG# (probe 2T)

SEQ ID NO: 16: *CTGGGGGCACCTGGGG# (probe 2C)

SEQ ID NO: 17: GGGTCCCGACTCTCAG (primer 2)

SEQ ID NO: 18: CTCCTAGTTCCTTTGAGC (primer 2')

SEQ ID NO: 19: *GGGCACTTGGGGAACTCATG# (probe 3T)

SEQ ID NO: 20: *GGGCACCTGGGGAACTCATG# (probe 3C)

SEQ ID NO: 21: GGGTCCCGACTCTCAGCC (primer 3)
```

```
SEQ ID NO: 22: TCTCCTAGTTCCTTTGAGC (primer 3')
SEQ ID NO: 23: *GGGCGCTGGGGGCACTTGG# (probe 4T)
SEQ ID NO: 24: *GGGCGCTGGGGGCACCTGG# (probe 4C)
SEQ ID NO: 25: GGGTCCCGACTCTCAGCCGC (primer 4)
SEQ ID NO: 26: CCGATCTCCTAGTTCCTTTGAGC (primer 4')
SEQ ID NO: 27: #TTCCCCAAGTGCCCC* (probe 5T)
SEQ ID NO: 28: #TTCCCCAGGTGCCCC* (probe 5C)
SEQ ID NO: 29: TCCTAGTTCCTTTGAGC (primer 5)
SEQ ID NO: 30: GGGTCCCGACTCTC (primer 5')
SEQ ID NO: 31: ATCTCCTAGTTCCTTTGAG (primer 6)
SEQ ID NO: 32: CGCTCGGGGTAACC (primer 6')
SEQ ID NO: 33: CCTAGTTCCTTTGAGC (primer 7)
SEQ ID NO: 34: GGGGTCCCGACTC (primer 7')
SEQ ID NO: 35: CTCCTAGTTCCTTTGAGC (primer 8)
SEQ ID NO: 36: CGCTCGGGGTAACC (primer 8')
SEQ ID NO: 37: #AGTTCCCCAAGTGCCCC* (probe 6T)
SEQ ID NO: 38: #AGTTCCCCAGGTGCCCC* (probe 6C)
SEQ ID NO: 39: TCCTAGTTCCTTTGAGC (primer 9)
SEQ ID NO: 40: GGGTCCCGACTCTC (primer 9')
SEQ ID NO: 41: ATCTCCTAGTTCCTTTGAG (primer 10)
SEQ ID NO: 42: CGCTCGGGGTAACC (primer 10')
SEQ ID NO: 43: CCTAGTTCCTTTGAGC (primer 11)
SEQ ID NO: 44: GGGGTCCCGACTC (primer 11')
SEQ ID NO: 45: CTCCTAGTTCCTTTGAGC (primer 12)
SEQ ID NO: 46: CGCTCGGGGTAACC (primer 12')
SEQ ID NO: 47: #TTCCCCAAGTGCCC* (probe 7T)
SEQ ID NO: 48: #TTCCCCAAGTGCCC* (probe 7C)
SEQ ID NO: 49: GATCTCCTAGTTCCTTTG (primer 13)
SEQ ID NO: 50: GGGTCCCGACTCTC (primer 13')
SEQ ID NO: 51: TCCTAGTTCCTTTGAGC (primer 14)
SEQ ID NO: 52: GGGTCCCGACTCTC (primer 14')
SEQ ID NO: 53: ATCTCCTAGTTCCTTTGAG (primer 15)
SEQ ID NO: 54: CGCTCGGGGTAACC (primer 15')
SEQ ID NO: 55: TCTCCTAGTTCCTTTGAGC (primer 16)
SEQ ID NO: 56: CCGGGCCGCCAAG (primer 16')
SEQ ID NO: 57: CCTAGTTCCTTTGAGC (primer 17)
SEQ ID NO: 58: GGGGTCCCGACTC (primer 17')
SEQ ID NO: 59: CTCCTAGTTCCTTTGAGC (primer 18)
SEQ ID NO: 60: CGCTCGGGGTAACC (primer 18')
SEQ ID NO: 61: CCGATCTCCTAGTTCCTTTG (primer 19)
SEQ ID NO: 62: CCGGGCCGCCAAG (primer 19')
SEQ ID NO: 63: ATCTCCTAGTTCCTTTGAGC (primer 20)
SEQ ID NO: 64: CGCTCGGGGTAACCG (primer 20')
SEQ ID NO: 65: GATCTCCTAGTTCCTTTG (primer 21)
SEQ ID NO: 66: GGGGTCCCGACTC (primer 21')
```

Other primer/probe sets can be designed based on the target region sequence, to include from between about 13 to about 40 nucleotides (primers) and from between about 12-25 nucleotides (probes) which span the −228 position in this region of GJB2 as described above, and sequences complementary to said sequences. Alternatively, primers may be designed based on sequence information further upstream or downstream from the target region sequence (SEQ ID NOs: 9, 10); i.e. upstream or downstream from bases −340 through −134) described above.

In addition, probes may be designed which vary from those shown above as SEQ ID NOs: 11-12, 15-16, 19-20, 23-24, 27-28, 37-38, and 47-48 (probes 1T/1C through 7T/7C) and sequences complementary thereto, as long as the sequence surrounding the possible target polymorphism is present in the probe. Thus, probes of the invention may comprise sequences from between 12 to 30 nucleotides that span the possible target polymorphism at position −228 from within target sequences SEQ ID NOs: 67 and 68 indicated below, and probes with sufficient sequence identity to SEQ ID NOs: 11-12, 15-16, 19-20, 23-24, 27-28, 37-38, and 47-48 to permit them to hybridize to said target sequences under standard or stringent conditions, and sequences complementary thereto:

```
SEQ ID NO: 67:
TAACCGGGGG AGACTCAGGG CGCTGGGGGC ACT/TGGGGAA
CTCATGGGGG CTCAAAGGAA CTAGGAGATC.

SEQ ID NO: 68:
TAACCGGGGG AGACTCAGGG CGCTGGGGGC ACCTGGGGAA
CTCATGGGGG CTCAAAGGAA CTAGGAGATC.
```

More particularly, probes of the invention comprise sequences from between 13 to 25 nucleotides spanning nucleotide −228 from within target sequences defined by SEQ ID NOs: 9, 10, 67 and 68, and probes with sufficient sequence identity to SEQ ID NOs: 11-12, 15-16, 19-20, 23-24, 27-28, 37-38, and 47-48 to permit them to hybridize to said target sequences under standard or stringent conditions, and sequences complementary thereto. Still more particularly, probes of the invention comprise a subsequence selected from:

```
SEQ ID NO: 69:
G G G G C A C T T G G G G (probe 8);

SEQ ID NO: 70:
T G G G G G C A C T T G G G G (probe 9);
```

-continued

SEQ ID NO: 71:
G G G G C A C T T G G G GAACTCA (probe 10);

SEQ ID NO: 72:
G G G G C A C C T G G G G (probe 11);

SEQ ID NO: 73:
G G G G G C A C CT G G G G A (probe 12);

SEQ ID NO: 74:
G C T G G G G G C A C C T G G (probe 13);

and sequences that are complementary to SEQ ID NOs: 69-74, as well as probes with sufficient sequence identity to SEQ ID NOs: 69-74 and complementary sequences thereto to permit them to hybridize to said target sequences (SEQ ID NOs: 9, 10, 67 and 68) under standard or stringent conditions.

Examples of protocols for real-time PCR are readily available in the literature, and included in product brochures from a number of biotechnology companies, such that one of skill in the art can design and optimize a particular protocol best-suited for the target DNA of interest, such as the polymorphism T-228C described herein. An example protocol includes Applied Biosystem's Protocol for the TaqMan® One-Step RT-PCR Master Mix Reagents Kit, copyright 2006, Applied Biosystems, as described in pp. 1-44 at http://www3.appliedbiosystems.com/cms/groups/mcb_support/documents/generaldocuments/cms_041056.pdf, as downloaded on Feb. 13, 2008, the contents of which are incorporated by reference herein.

Detection of more than one polymorphism within a given sequence may be achieved using sequential PCR techniques as described above, or may be done in one analysis using multiplex PCR. One example of multiplex PCR uses a single primer that is specific to the target area and another primer that is common for all targets. The common primer corresponds to adapters attached to both ends of each DNA fragment. Because the common primer is rich in two of DNA's bases, guanine and cytosine, which results in an especially strong base pair, the DNA fragments form hairpin structures, with the target DNA forming a loop. Thus, only half the number of primers needs to be engineered to amplify multiple targets on a strand of DNA. This type of multiplex PCR ideally provides more reliable amplification of multiple segments of DNA at the same time, and is also highly specific because it occurs within narrower temperature constraints than traditional PCR. This type of multiplex PCR is described in PNAS (N. Broude et al., "Multiplex allele-specific target amplification based on PCR suppression", PNAS 2001 98: 206-211, the entire contents of each which is hereby incorporated by reference herein.

Examples of multiplex PCR methodology are described by Henegariu et al, "Multiplex PCR: Critical Parameters and Step-by-Step Protocol, *BioTechniques* 23: 504-511 (1997); Löffert et al, "Optimization of Multiplex PCR", *Qiagen News*, issue no. 2, 1999, Reader Inquiry No. 99204, Qiagen.com; (http://www 1.qiagen.com/literature/qiagennews/0299/992optim.pdf#search=%22multiplex % 20 pcr %20optimization %22); by O. Henegariu at http://www.m-ed.yale.edu/genetics/ward/tavi/p04.html (Multiplex Priming Pairs); and in Applied Biosystems (AB) protocol 104GU02-01 (part number 4371091 Revision C), of which the entire contents of each is hereby incorporated by reference herein.

Multiplex PCR is also suitable for use in bioarrays, wherein probes for target polymorphisms are hybridized to a chip, and the single chip may simultaneously test for multiple different polymorphisms and mutations in a single PCR reaction. From that single chip it is possible to obtain read-out on multiple sequences. Examples of this technology is describe by C. Børsting et al, Multiplex PCR, amplicon size and hybridization efficiency on the NanoChip electronic microarray" *Int J Legal Med,* 118: 75-82 (2004); and by A. Jääskeläinen, et al., "Multiplex-PCR and oligonucleotide microarray for detection of eight different herpesviruses from clinical specimens", *J Clin Virol,* 37 (2), 83-90, the entire contents of which are hereby incorporated by reference herein.

As is well known in genetics, nucleotide and amino acid sequences obtained from different sources for the same gene may vary both in the numbering scheme and in the precise sequence. Such differences may be due to inherent sequence variability within the gene and/or to sequencing errors. Accordingly, reference herein to a particular polymorphic site by number (e.g., 35delG, GJB2 T101C (M34T) and others) will be understood by those of skill in the art to include those polymorphic sites that correspond in sequence and location within the gene, even where different numbering/nomenclature schemes are used to describe them.

Sequence Table 1941_B22
Table of Sequences FOR 1941/B22

| SEQ ID NO | Description | Length | Type |
|---|---|---|---|
| 1 | primer | 20 | DNA |
| 2 | primer | 20 | DNA |
| 3 | primer | 19 | DNA |
| 4 | primer | 20 | DNA |
| 5 | primer | 30 | DNA |
| 6 | probe | 30 | DNA |
| 7 | probe | 39 | DNA |
| 8 | probe | 39 | DNA |
| 9 | GJB2 target sequence | 207 | DNA |
| 10 | GJB2 target sequence | 207 | DNA |
| 11 | probe 1T | 16 | DNA |
| 12 | probe 1C | 16 | DNA |
| 13 | primer 1 | 34 | DNA |
| 14 | primer 1' | 31 | DNA |
| 15 | probe 2T | 16 | DNA |
| 16 | probe 2C | 16 | DNA |
| 17 | primer 2 | 30 | DNA |
| 18 | primer 2' | 34 | DNA |
| 19 | probe 3T | 20 | DNA |
| 20 | probe 3C | 20 | DNA |
| 21 | primer 3 | 37 | DNA |
| 22 | primer 3' | 35 | DNA |
| 23 | probe 4T | 18 | DNA |
| 24 | probe 4C | 19 | DNA |
| 25 | primer 4 | 34 | DNA |
| 26 | primer 4' | 33 | DNA |
| 27 | probe 5T | 15 | DNA |
| 28 | probe 5C | 15 | DNA |
| 29 | primer 5 | 17 | DNA |
| 30 | primer 5' | 14 | DNA |
| 31 | primer 6 | 19 | DNA |
| 32 | primer 6' | 14 | DNA |
| 33 | primer 7 | 16 | DNA |
| 34 | primer 7' | 13 | DNA |
| 35 | primer 8 | 18 | DNA |
| 36 | primer 8' | 14 | DNA |
| 37 | probe 6T | 17 | DNA |
| 38 | probe 6C | 17 | DNA |
| 39 | primer 9 | 17 | DNA |
| 40 | primer 9' | 14 | DNA |
| 41 | primer 10 | 19 | DNA |
| 42 | primer 10' | 14 | DNA |
| 43 | primer 11 | 16 | DNA |
| 44 | primer 11' | 13 | DNA |
| 45 | primer 12 | 18 | DNA |
| 46 | primer 12' | 14 | DNA |
| 47 | probe 7T | 14 | DNA |
| 48 | probe 7C | 14 | DNA |
| 49 | primer 13 | 18 | DNA |
| 50 | primer 13' | 14 | DNA |

Sequence Table 1941_B22
Table of Sequences FOR 1941/B22

| SEQ ID NO | Description | Length | Type |
|---|---|---|---|
| 51 | primer 14 | 17 | DNA |
| 52 | primer 14' | 14 | DNA |
| 53 | primer 15 | 19 | DNA |
| 54 | primer 15' | 14 | DNA |
| 55 | primer 16 | 19 | DNA |
| 56 | primer 16' | 13 | DNA |
| 57 | primer 17 | 16 | DNA |
| 58 | primer 17' | 13 | DNA |
| 59 | primer 18 | 18 | DNA |
| 60 | primer 18' | 14 | DNA |
| 61 | primer 19 | 20 | DNA |
| 62 | primer 19' | 13 | DNA |
| 63 | primern 20 | 20 | DNA |
| 64 | primer 20' | 15 | DNA |
| 65 | primer 21 | 18 | DNA |
| 66 | primer 21' | 13 | DNA |
| 67 | GJB2 target sequence | 70 | DNA |
| 68 | GJB2 target sequence | 70 | DNA |
| 69 | probe 8 | 13 | DNA |
| 70 | probe 9 | 15 | DNA |
| 71 | probe 10 | 19 | DNA |
| 72 | probe 11 | 13 | DNA |
| 73 | probe 12 | 15 | DNA |
| 74 | probe 13 | 15 | DNA |

What is claimed is:

1. A method of identifying a subject at risk for developing non-syndromic hearing impairment (NSHI) comprising:

obtaining a sample of DNA from a subject;

detecting in said sample of DNA allelic forms of a first polymorphism in gap junction beta 2 (GJB2) gene of chromosome 13 at position −228, said position located in a promoter region of the GJB2 gene; and identifying a subject having a homozygous "C" genotype for a polymorphism at position −288 of the GJB2 gene as a subject who is at increased risk for NSHI as compared to a subject with no "C" genotype at that position, said polymorphism at position −288 of the GJB2 gene comprised within a nucleotide sequence selected from the group consisting of SEQ ID NO: 8, SEQ ID NO: 10, SEQ ID NO: 12, SEQ ID NO: 16, SEQ ID NO: 20, SEQ ID NO: 24, SEQ ID NO: 28, SEQ ID NO: 38, SEQ ID NO: 48, SEQ ID NO: 68, SEQ ID NO: 72, SEQ ID NO: 73, SEQ ID NO: 74, and sequences that are complementary to said sequences.

2. A method according to claim 1, further comprising:

detecting in said sample allelic forms of a second polymorphism in the GJB2 gene of chromosome 13, wherein a subject having a homozygous C genotype at said position −228 of the GJB2 gene and a heterozygous genotype for the second polymorphism is at increased risk for NSHI compared to a subject with no C genotype at said position −228.

3. A method according to claim 2, wherein the second polymorphism is selected from the group consisting of 35delG, G154C/V52L, C249G/F83L, G262T/A88S, T269C/L90P, G380A/R127H and G457A/V153I.

4. A method according to claim 3, wherein the second polymorphism is 35delG.

5. A method according to claim 2, wherein the second polymorphism is G457A/V153I.

6. A method according to claim 5, further comprising detecting in said sample allelic forms of a third polymorphism, wherein the third polymorphism is 35delG.

7. A method according to claim 1, wherein the subject is a member of a family having at least one member diagnosed with non-syndromic hearing impairment.

8. A method according to claim 1 wherein the subject is an infant from zero to 24 months.

9. A method according to claim 1 wherein the subject is a person from age 24 months to 95.

10. A method according to claim 1 or 8 wherein detecting further comprises:
    amplifying the GJB2 gene sequence having a transcription start site;
    retrieving a DNA sequence region proximal to the GJB2 transcription start site;
    amplifying a region between −427 and IVS 1 243 of the GJB2 locus to produce amplified DNA products; and
    sequencing the amplified DNA products.

11. A method according to claim 10, wherein the amplifying step is performed using polymerase chain reaction (PCR) technology.

12. A method according to claim 11, wherein the PCR technology is real time PCR technology.

13. A method according to claim 11, wherein the PCR technology is multiplex PCR technology.

14. A method according to claim 11, wherein the PCR technology is molecular beacon PCR technology.

15. A method according to claim 11, wherein the PCR technology is allele specific PCR technology.

16. A method according to claim 11, wherein the PCR technology is amplification refractory mutation system (ARMS).

17. A method according to claim 1, wherein the detection step is performed using restriction fragment length polymorphism analysis.

* * * * *